United States Patent
Gieffers et al.

(10) Patent No.: US 10,683,332 B2
(45) Date of Patent: Jun. 16, 2020

(54) SINGLE-CHAIN LIGHT RECEPTOR AGONIST PROTEINS

(71) Applicant: Apogenix AG, Heidelberg (DE)

(72) Inventors: Christian Gieffers, Dossenheim (DE);
Oliver Hill, Neckarsteinach (DE);
Meinolf Thiemann, Schriesheim (DE);
Tim Schnyder, Igersheim (DE)

(73) Assignee: Apogenix AG, Heidelberg (DE)

( * ) Notice: Subject to any disclaimer, the term of this patent is extended or adjusted under 35 U.S.C. 154(b) by 0 days.

(21) Appl. No.: 15/958,707

(22) Filed: Apr. 20, 2018

(65) Prior Publication Data

US 2018/0251509 A1 Sep. 6, 2018

Related U.S. Application Data

(63) Continuation of application No. PCT/EP2016/075536, filed on Oct. 24, 2016.

(60) Provisional application No. 62/245,943, filed on Oct. 23, 2015.

(51) Int. Cl.
| | | |
|---|---|---|
| C07K 14/52 | (2006.01) | |
| C07K 16/46 | (2006.01) | |
| C07H 21/04 | (2006.01) | |
| C12N 15/63 | (2006.01) | |
| A61P 35/00 | (2006.01) | |

(52) U.S. Cl.
CPC .............. *C07K 14/52* (2013.01); *A61P 35/00* (2018.01); *C07K 2319/02* (2013.01); *C07K 2319/30* (2013.01)

(58) Field of Classification Search
None
See application file for complete search history.

(56) References Cited

U.S. PATENT DOCUMENTS

| 9,908,927 B2 | 3/2018 | Hill et al. |
| 2009/0232808 A1 | 9/2009 | Priest et al. |

FOREIGN PATENT DOCUMENTS

| WO | 01/25277 A1 | 4/2001 |
| WO | 01/49866 A1 | 7/2001 |
| WO | 02/09055 A1 | 1/2002 |
| WO | 2004085478 A2 | 10/2004 |
| WO | 2005103077 A1 | 11/2005 |
| WO | 2006/079176 | 8/2006 |
| WO | 2010/010051 | 1/2010 |
| WO | 2015/164588 | 10/2015 |
| WO | 2016/146818 | 9/2016 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Jung-Hwan Lee et al, "Biochemical characterization of a new recombinant TNF receptor-hyFc fusion protein expressed in CHO cells", Protein Expression and Purification, Jan. 1, 2013, pp. 17-26, vol. 87, No. 1, San Diego, US.
International Search Report dated Jan. 23, 2017 issued in PCT/EP2016/075536.
Tetsuya Shiraishi, et al., "Increased cytotoxicity of soluble Fas ligand by fusing isoleucine zipper motif", Biochemical and Biophysical Research Communications 322 (2004) 197-202.
Pascal Schneider, et al., "Conversion of Membrane-bound Fas(CD95) Ligand to Its Soluble Form Is Associated with Downregulation of Its Proapoptotic Activity and Loss of Liver Toxicity", J. Exp. Med., vol. 187, No. 8, Apr. 20, 1998, pp. 1205-1213.

* cited by examiner

*Primary Examiner* — Christine J Saoud
*Assistant Examiner* — Jon M Lockard
(74) *Attorney, Agent, or Firm* — Viola T. Kung; Perkins Coie LLP

(57) ABSTRACT

Provided herein are specific LIGHT receptor agonist proteins, nucleic acids encoding the same, and methods of treating a subject having a LIGHT-associated disease or disorder. The LIGHT receptor agonist proteins provided herein comprise three soluble LIGHT domains and an Fc fragment. The LIGHT receptor agonist proteins are substantially non-aggregating and suitable for therapeutic, diagnostic and/or research applications.

10 Claims, 6 Drawing Sheets
Specification includes a Sequence Listing.

Figure 6: Analytical size exclusion chromatography of PROTEIN A (A) and a PROTEIN B (B) performed on a 1260 infinity HPLC system using a Tosoh TSKgelG3000SWxl column. The column was loaded with protein at a concentration of 0.94 mg/ml (A) or 0.77 mg/ml (B) in a total volume of 20 µl. The flow rate was set to 0.5 ml/min. One observes a single main peak at 16.239 (A) and 15.842 min (B).

US 10,683,332 B2

SINGLE-CHAIN LIGHT RECEPTOR AGONIST PROTEINS

This application is a continuation of PCT/EP2016/075536, filed Oct. 24, 2016; which claims priority to U.S. Provisional Application No. 62/245,943, filed Oct. 23, 2015. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Apr. 19, 2018, and a size of 95.8 kilobytes. The Sequence Listing filed via EFS-Web is part of the specification and is hereby incorporated in its entirety by reference herein.

FIELD OF THE INVENTION

The present invention provides specific LIGHT receptor agonist proteins comprising three soluble LIGHT domains and an Fc fragment, nucleic acid molecules encoding the LIGHT receptor agonist proteins, and uses thereof. The LIGHT receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

There is a need in the art for novel LIGHT receptor agonists that exhibit high biological activity independent of Fc-gamma-R based crosslinking in vivo, high stability, and allow for efficient recombinant manufacturing. Additionally, there is need in the art for enabling technologies to create human LIGHT-receptor selective biologics as human LIGHT has to at least three interaction partners in vivo: LT-beta-R, DcR3 and HVEM.

SUMMARY OF THE INVENTION

The present invention provides specific LIGHT receptor agonist proteins that mimic the LIGHT-receptor(s):LIGHT interaction in vivo, exhibit low proteolytic degradation and a shorter in vivo half-life as compared to agonistic monoclonal antibodies.

The LIGHT receptor agonist proteins of the instant invention generally comprise: (i) a first soluble LIGHT cytokine domain; (ii) a first peptide linker; (iii) a second soluble LIGHT domain; (iv) a second peptide linker; (v) a third soluble LIGHT domain; (vi) a third peptide linker (e.g., a hinge-linker) and (vii) an antibody Fc fragment.

In one embodiment, the antibody Fc fragment (vii) is located N terminal to the first LIGHT domain (i) and/or C-terminal to the third LIGHT domain (v). In another embodiment the antibody Fc fragment is located C-terminally to the third LIGHT domain (v). In one embodiment, the polypeptide is substantially non-aggregating. In another embodiment, the second and/or third soluble LIGHT domain is an N-terminally shortened domain which optionally comprises amino acid sequence mutations.

In one embodiment, at least one of the soluble LIGHT domains, particularly at least one of the soluble LIGHT domains (iii) and (v), is a soluble LIGHT domain with an N-terminal sequence which starts at amino acid Glu91 or Asn93 or Pro94 of human LIGHT and wherein Glu91 or Asn93 or Pro94 may be replaced by a neutral amino acid, e.g., Ser or Gly. In another embodiment, at least one of the soluble LIGHT domains, particularly at least one of the soluble LIGHT domains (iii) and (v), is a soluble LIGHT domain with an N-terminal sequences selected from (a) Asn93-Ala95 and (b) (Gly/Ser)93-Ala95. In one embodiment, the soluble LIGHT domain ends with amino acid Val240 of human LIGHT and/or optionally comprises one or more mutation at positions: N93, N102, E115, T116, Q117, L118, G119, L120, C154, R172, Y173, E175, E176, E178, C187, R228, D229. In one embodiment, the soluble LIGHT domains (i), (iii) and (v) comprise amino acids Glu91-Val240 of human LIGHT according to SEQ ID NO: 01.

In one embodiment, at least one of the soluble LIGHT domains, particularly at least the soluble LIGHT domains (i), is a soluble LIGHT domain with an N-terminal sequence which starts at amino acid Glu91 and wherein Glu91 may be replaced by Gln.

In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO: 2. In another embodiment, the polypeptide additionally comprises an N-terminal signal peptide domain, e.g., of SEQ ID NO: 17, which may comprise a protease cleavage site, and/or which additionally comprises a C-terminal element which may comprise and/or connect to a recognition/purification domain, e.g., a Strep-tag attached to a serine linker according to SEQ ID NO: 18.

In one embodiment, the antibody Fc fragment (vii) is fused to the soluble LIGHT domain (i) and/or (v) via a hinge-linker, preferably of SEQ ID NO: 16. In another embodiment, the antibody Fc fragment (vii) consists of the amino acid sequence as shown in SEQ ID NO: 13 or 14.

In one embodiment, the single-chain fusion polypeptide of the present invention comprises the amino acid sequence selected from the group consisting of SEQ ID NO: 15, and 25-32.

In one embodiment, the present invention provides a LIGHT receptor agonist protein comprising a dimer of two single-chain fusion polypeptides each having the amino acid sequence set forth in SEQ ID NO: 27. In one embodiment, the two polypeptides are covalently linked through three interchain disulfide bonds formed between cysteine residues 468, 474, and 477 of each polypeptide.

In one embodiment the asparagine residue at position 156 of the mature polypeptide(s) SEQ ID NO: 27, 28, 29, 30, and 32 is N-glycosylated.

In another embodiment, the asparagine residues at positions 156 and 312 of the polypeptide SEQ ID NO: 31 are both N-glycosylated.

In another embodiment, the polypeptide(s) are further post-translationally modified. In another embodiment, the post-translational modification comprises the N-terminal glutamine of the E91Q mutein modified to pyroglutamate.

DETAILED DESCRIPTION OF THE INVENTION

The present invention provides a single-chain fusion polypeptide comprising at least three soluble LIGHT domains connected by two peptide linkers and N-terminally and/or C-terminally an antibody-derived dimerization domain. The inventors have discovered that dimerization of the two single-chain fusion polypeptides through the dimerization domain results in a hexavalent LIGHT receptor agonist, which provides high biological activity and good stability.

Preferably, the single-chain fusion polypeptide is non-aggregating. The term "non-aggregating" refers to a monomer content of the preparation of ≥50%, preferably ≥70% and more preferably ≥90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the "monomer" content is as defined above after a time period of several days, e.g. 10 days, more preferably after several weeks, e.g. 2, 3 or 4 weeks, and most preferably after several months, e.g. 2 or 3 months of storage at 4° C., or 25° C. With regard to the definition of "monomer" in the case of FC-fusion proteins, the assembly of two polypeptide chains is driven by the FC-part and the functional unit of the resulting assembled protein consists of two chains. This unit is defined as "monomer" in the case of Fc-fusion proteins regardless of being a dimerized single-chain fusion polypeptide.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 18.

The LIGHT receptor agonist protein of the present invention comprises three soluble domains derived from LIGHT. Preferably, those soluble domains are derived from a mammalian, particularly human LIGHT including allelic variants and/or derivatives thereof. The soluble domains comprise the extracellular portion of LIGHT including the receptor binding domain without membrane located domains. Like other proteins of the TNF superfamily, LIGHT is anchored to the membrane via anN-terminal portion of 15-30 amino acids, the so-called stalk-region. The stalk region contributes to trimerization and provides a certain distance to the cell membrane. However, the stalk region is not part of the receptor binding domain (RBD).

Figure 1:
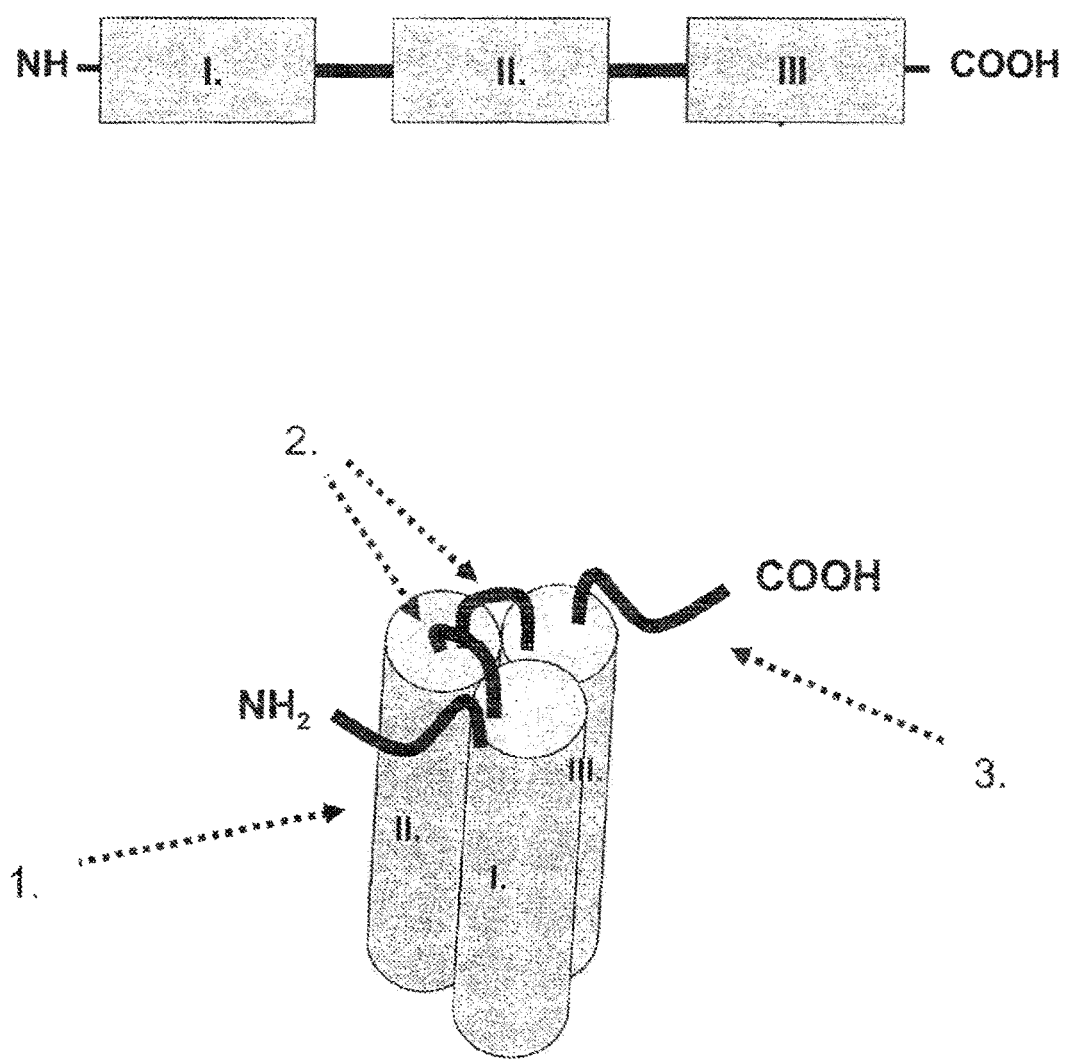
FIG. 1 Domain structure of a single-chain fusion polypeptide comprising three LIGHT domains. I., II., III. Soluble LIGHT domains.
Figure 2:
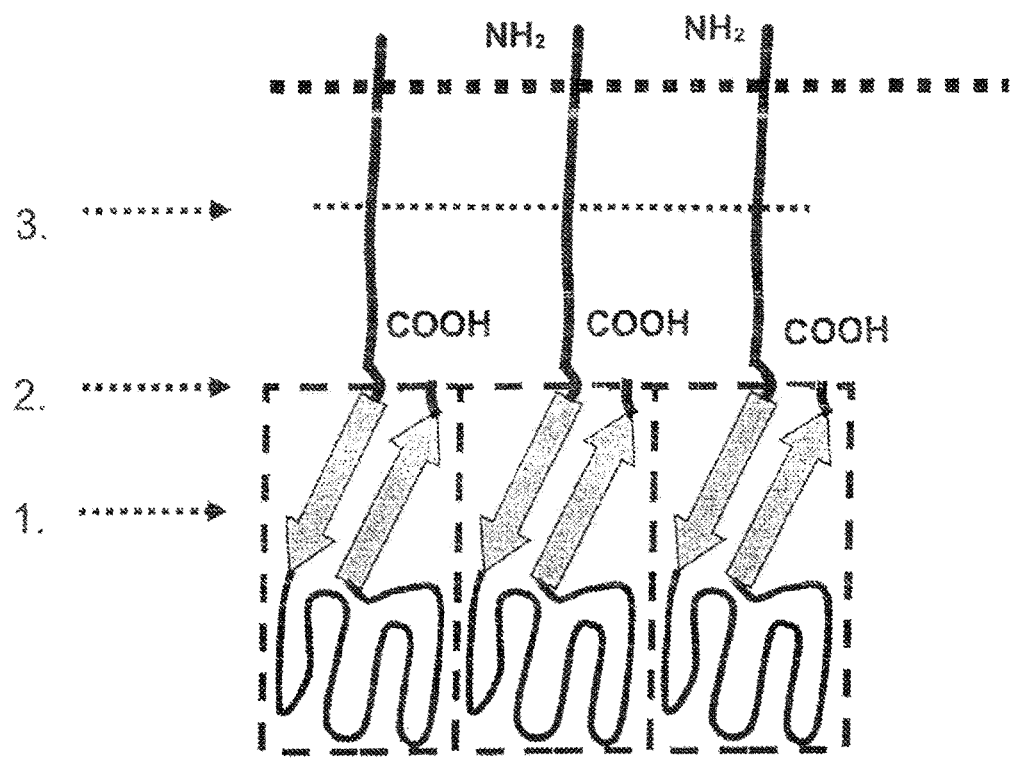
FIG. 2 Schematic picture representing the general structure of LIGHT.
▓ ▓ ▓ Cell membrane, N-terminus located within the cell,
1. anti-parallel β-fold of receptor-binding domain (RBD),
2. interface of RBD and cell membrane,
3. protease cleavage site.
Figure 3:
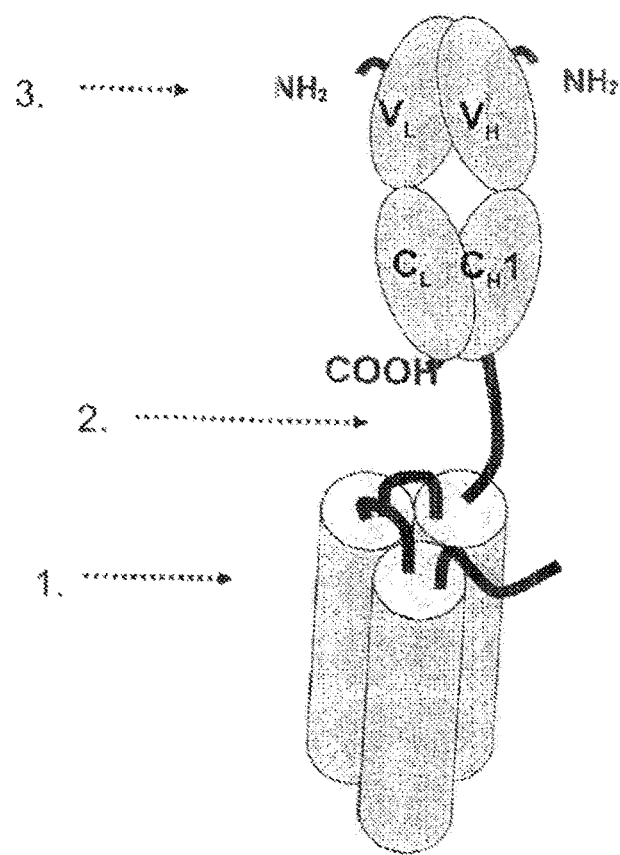
FIG. 3 Single-chain fusion polypeptide comprising an additional Fab antibody fragment.
Figure 4:
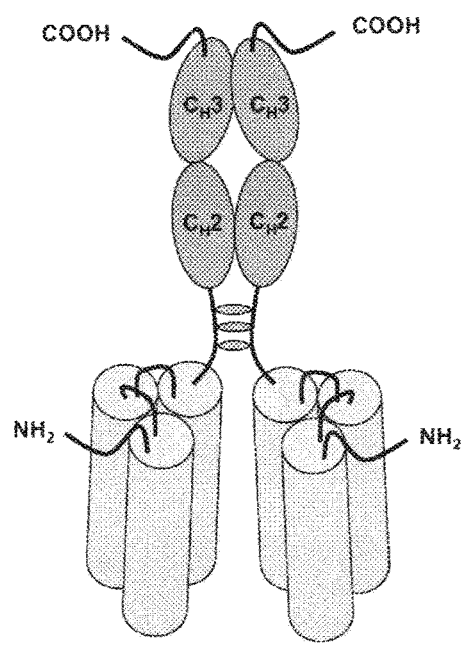
FIG. 4 Dimerization of two C-terminally fused scFc fusion polypeptides via three disulfide bridges.

Importantly, the RBD is characterized by a particular localization of its N- and C-terminal amino acids. Said amino acids are immediately adjacent and are located centrally to the axis of the trimer. The first N-terminal amino acids of the RBD form an anti-parallel beta-strand with the C-terminal amino acids of the RBD (FIG. 2).

Thus, the anti-parallel beta-strand of the RBD forms an interface with the cell membrane, which is connected to and anchored within the cell membrane via the amino acids of the stalk region. It is highly preferred that the soluble LIGHT domains of the LIGHT receptor agonist protein comprise a receptor binding domain of the LIGHT lacking any amino acids from the stalk region. Otherwise, a long linker connecting the C-terminus of one of the soluble domains with theN-terminus of the next soluble domain would be required to compensate for the N-terminal stalk-region of the next soluble domain, which might result in instability and/or formation of aggregates.

A further advantage of such soluble domains is that the N-terminal amino acids of the RBD are not accessible for any anti-drug antibodies. Preferably, the single-chain fusion polypeptide consisting of (i) a first soluble LIGHT cytokine domain; (ii) a first peptide linker; (iii) a second soluble LIGHT domain; (iv) a second peptide linker; (v) a third soluble LIGHT domain is capable of forming an ordered structure mimicking the trimeric organization of its natural counterpart thereby comprising at least one functional binding site for the respective LIGHT receptor. The single-chain fusion polypeptide comprising components (i)-(v) is therefore also termed single-chain-LIGHT-receptor-binding-domain (scLIGHT-RBD).

The LIGHT receptor agonist protein comprises three functional LIGHT-receptor binding sites, i.e. amino acid sequences capable of forming a complex with a LIGHT-receptor. Thus, the soluble domains are capable of binding to the corresponding LIGHT-receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble LIGHT domain may be derived from human LIGHT as shown in SEQ ID NO: 1. Preferably, the soluble LIGHT domains are derived from human LIGHT, particularly starting from amino acids 91 or 94 and comprise particularly amino acids 91-240 or 94-240 of SEQ ID NO: 1. Optionally, amino acid Glu91 of SEQ ID NO: 1 may be replaced by a non-charged amino acid, e.g. Ser or Gly or is replaced by Glutamine.

TABLE 1

Sequence of Wild-Type Human LIGHT Protein

| SEQ ID NO | Sequence |
|---|---|
| 1 | MEESVVRPSVFVVDGQTDIPFTRLGRSHRRQSCSVARVGLGLLL LLMGAGLAVQGWFLLQLHWRLGEMVTRLPDGPAGSWEQLIQERR SHEVNPAAHLTGANSSLTGSGGPLLWETQLGLAFLRGLSYHDGA LVVTKAGYYYIYSKVQLGGVGCPLGLASTITHGLYKRTPRYPEE LELLVSQQSPCGRATSSSRVWWDSSFLGGVVHLEAGEEVVVRVL DERLVRLRDGTRSYFGAFMV |

As indicated above, the soluble LIGHT domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains that cannot bind to the corresponding cytokine receptor can be selected.

In a further embodiment of the invention, the soluble LIGHT domain (i) comprises a mutant of LIGHT or a receptor binding domain thereof resulting in reduced affinity and/or reduced activation of LIGHT-receptor.

LIGHT-Muteins Affecting Receptor Binding and/or Activity

The mutant may be generated by any technique known by a skilled person. The substitution may affect at least one amino acid of LIGHT, e.g., human LIGHT (e.g., SEQ ID NO: 1) or a receptor binding domain thereof as described herein. Preferred substitutions in this regard affect at least one of the following amino acids of human LIGHT of SEQ ID NO: 1: E115, T116, Q117, L118, G119, L120, R172, Y173, E175, E176, E178, R228, D229. In a preferred embodiment Y173 is mutated to S, T, D, E, R or F.

Human LIGHT has at least three different receptors/interaction partners in vivo, namely LT-beta-R, DcR3 and HVEM. The amino acid substitution(s) may affect the binding and/or activity of LIGHT, e.g., human LIGHT, to or on either the LIGHT-receptor(s) binding or the LIGHT-receptor(s) induced signaling. The binding and/or activity of the LIGHT-receptor may be affected positively, i.e., stronger, more selective or more specific binding and/or more activation of the receptor. Alternatively, the binding and/or activity of the LIGHT-receptor may be affected negatively, i.e., weaker, less selective or less specific binding and/or less or no activation of the receptor or receptor(s).

Thus one embodiment is a LIGHT receptor agonist protein as described herein wherein at least one of the soluble domains comprises a mutant of LIGHT or a receptor binding domain thereof which binds and/or activates LIGHT-receptor(s) to a lesser extent than the wildtype-LIGHT.

The single-chain fusion molecule of the present invention comprises three soluble LIGHT domains, namely components (i), (iii) and (v). The stability of a single-chain LIGHT fusion polypeptide against aggregation is enhanced, if the second and/or third soluble LIGHT domain is an N-terminally shortened domain which optionally comprises amino acid sequence mutations. Thus, preferably, both the second and the third soluble LIGHT domain are N-terminally shortened domains which optionally comprise amino acid sequence mutations in the N-terminal regions, preferably within the first five amino acids of the N-terminus of the soluble LIGHT domain. These mutations may comprise replacement of basic amino acids, by neutral amino acids, particularly serine or glycine.

In contrast thereto, the selection of the first soluble LIGHT domain is not as critical. Here, a soluble domain having a full-length N-terminal sequence may be used. It should be noted, however, that also the first soluble LIGHT domain may have an N-terminally shortened and optionally mutated sequence.

In a further preferred embodiment of the present invention, the soluble LIGHT domains (i), (iii) and (v) are soluble human LIGHT domains. The first soluble LIGHT domain (i) may be selected from native, shortened and/or mutated sequences. Thus, the first soluble LIGHT domain (i) has an N-terminal sequence which may start at amino acid Glu91 or Ala95 of human LIGHT, and wherein Glu91 may be replaced by a neutral amino acid, e.g. by Ser or Gly or by Gln to enable pyroglutamate formation during expression. The second and third soluble LIGHT domains (iii) and (v) have a shortened N-terminal sequence which preferably starts with amino acid Asn93 or Pro94 of human LIGHT (SEQ ID NO:1) and wherein Asn93 may be replaced by another amino acid, e.g. Ser or Gly.

Preferably, the N-terminal sequence of the soluble LIGHT domains (iii) and (v) is selected from:
(a) Asn93 or Pro94
(b) (Gly/Ser) 93.

The soluble LIGHT domain preferably ends with amino acid V240 of human LIGHT. In certain embodiments, the LIGHT domain may comprise internal mutations as described above.

Components (ii) and (iv) of the LIGHT receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition, it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylate site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the LIGHT agonist proteins and/or in order to reduce the potential immunogenicity, it may be preferred that linker (ii) or linker (iv) or both comprise a glycosylation site.

Preferred linker sequences are shown in Table 2. A preferred linker is GSGSGNGS (SEQ ID NO: 2). Another preferred linker is GSGS (SEQ ID NO:11).

TABLE 2

Example Linker Sequences

| SEQ ID NO | Sequence |
|---|---|
| 2 | GSGSGNGS |
| 3 | GSGSGSGS |

TABLE 2-continued

Example Linker Sequences

| SEQ ID NO | Sequence |
|---|---|
| 4 | GGSGSGSG |
| 5 | GGSGSG |
| 6 | GGSG |
| 7 | GGSGNGSG |
| 8 | GGNGSGSG |
| 9 | GGNGSG |
| 10 | GSGSGS |
| 11 | GSGS |
| 12 | GSG |

The LIGHT receptor agonist protein additionally comprises an antibody Fc fragment domain which may be located N-terminal to the first LIGHT domain (i) and/or C-terminal to the third LIGHT domain (v). Preferably, the antibody Fc fragment domain comprises a reduced capability to interact with Fc-gamma-R receptors in vivo. Preferably, the antibody Fc fragment domain comprises or consists of an amino acid sequence as shown in SEQ ID NO: 13 or 14 (see Table 3). Sequence ID NO: 13 has N297S mutation compared to wildtype human IGG1-Fc and does not bind to Fc-gamma-R receptors. Sequence ID NO: 14 is a glycosylated (N297 wildtype) human IGG1 Fc mutein with reduced Fc-gamma-R binding capability.

TABLE 3

Examples of Fc Fragment Domains

| SEQ ID NO | Sequence |
|---|---|
| 13 | PAPELLGGPSVFLFPPKPKDTLMISRTPEVTCVVVDVSHEDPE VKFNWYVDGVEVHNAKTKPREEQYSSTYRVVSVLTVLHQDWLN GKEYKCKVSNKALPAPIEKTISKAKGQPREPQVYTLPPSREEM TKNQVSLTCLVKGFYPSDIAVEWESNGQPENNYKTTPPVLDSD GSFFLYSKLTVDKSRWQQGNVFSCSVMHEALHNHYTQKSLSLS PGK |
| 14 | PAPPVAGPSVFLFPPKPKDTLMISRTPEVTCVVVDVSHEDPEV KFNWYVDGVEVHNAKTKPREEQYNSTYRVVSVLTVLHQDWLNG KEYKCKVSNKGLPSSIEKTISKAKGQPREPOVYTLPPSREEMT KNQVSLTCLVKGFYPSDIAVEWESNGQPENNYKTTPPVLDSDG SFFLYSKLTVDKSRWQQGNVFSCSVMHEALHNHYTQKSLSLSP GK |

Number of Glycosylation Sites and In Vivo Stability

The total number of glycosylation sites and the individual position of the carbohydrates in three dimensions impacts the in-vivo stability of LIGHT receptor agonist proteins. Further, carbohydrate recognition depends on local density of the terminal saccharides, the branching of the carbohydrate tree and the relative position of the carbohydrates to each other matter.

Further, partially degraded carbohydrates reduce the in vivo half-life of LIGHT receptor agonist proteins through lectin-driven mechanisms. By reducing the total number of glycosylation sites and/or their relative position on the molecule's surface, the resulting to compound is less accessible to these mechanisms, increasing half-life. In a preferred embodiment, the first linker (ii) is glycosylated and the second linker (iv) is not glycosylated to avoid carbohydrate patterns in close proximity on the proteins accessible surface. In a preferred embodiment, the linkers with (SEQ ID NO: 2) and (SEQ ID NO: 11) are combined in one scLIGHT-RBD module.

Depletion of antibody CH2-domain carbohydrates is necessary in order to avoid Fc-receptor based crosslinking in vivo and potential LIGHT-receptor superclustering-based toxicity. Also, unwanted Fc-driven mechanisms like ADCC could lead to toxic events. Accordingly, in one embodiment, the overall number of glycosylation sites on the LIGHT receptor agonist proteins of the instant invention is reduced through the depletion of CH2 glycosylation sites, particularly the N-glycosylation site, resulting in LIGHT receptor agonist proteins comprising N297S equivalent mutations of SEQ ID NO: is (PROTEIN A) (according to the EU numbering system) creating aglycosl-CH2 domains. In another embodiment of the invention, one or more of the soluble LIGHT domains (i), (iii), and (v) may comprise a N102 exchanged to aspartate, serine or glycine resulting in LIGHT receptor agonistic fusion proteins with a further reduced number of glycosylation sites. In a preferred embodiment, the N102 [D,S,G] mutation is restricted to the soluble LIGHT domains (iii) and (v) of the agonistic LIGHT receptor agonistic fusion proteins of the present invention.

CH2-domain Destabilization is Compensated by an Additional Hinge-cysteine

Figure 5:
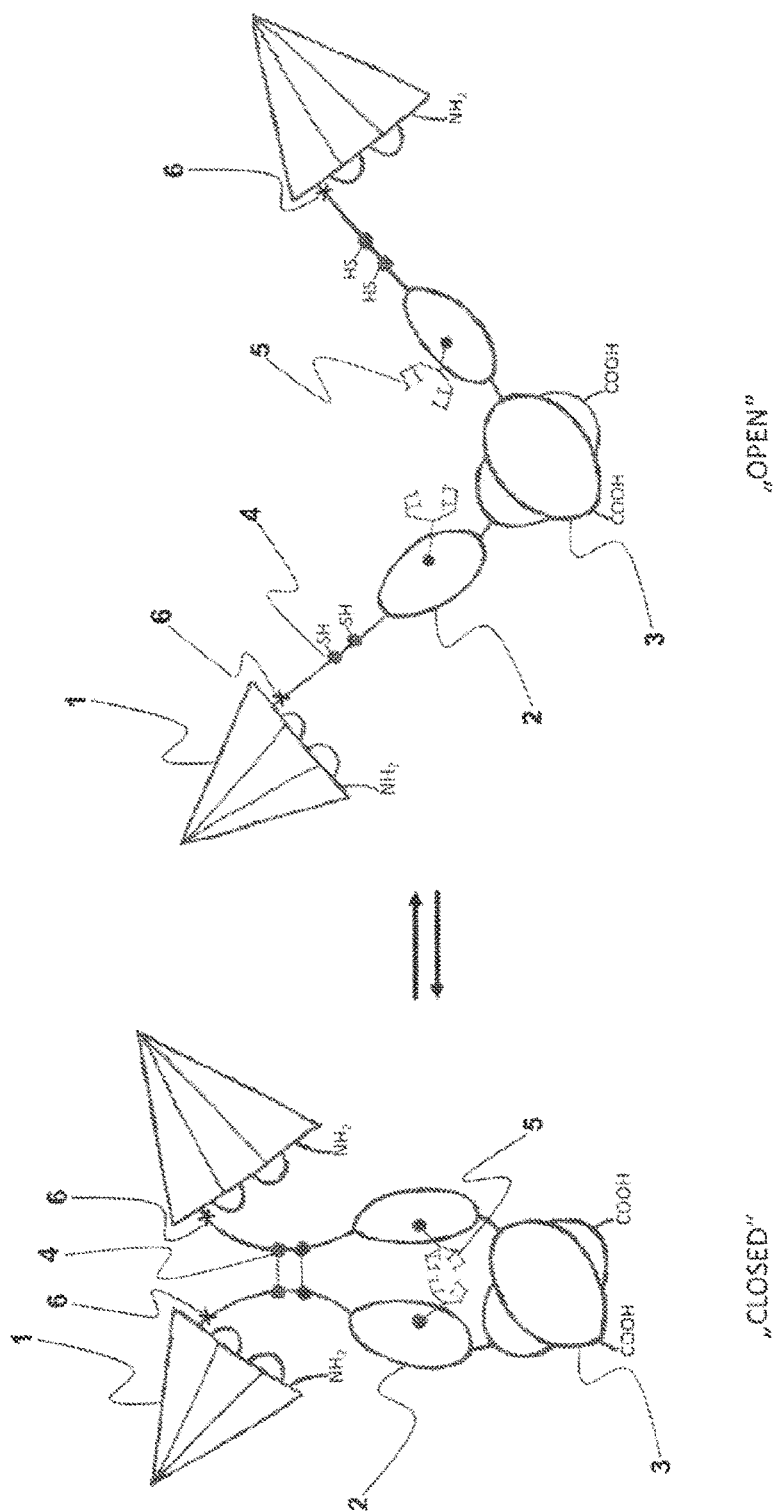
FIG. 5 Schematic representation of the hexavalent single chain LIGHT receptor agonist fusion protein of the invention. CH2-Carbohydrates (5) present on the inner surface areas normally shield the CH2-subdomain sterically (2) from proteases during "open Fc-conformation transits" wherein hinge-interchain disulfide bonds (4) are reduced and the covalent interchain linkage is disrupted. This enables CH2-dissociation and exposure of the inner surface areas and the upper hinge lysine K223 (6) towards proteases. Dimer association in the "open stage" remains intact due to the high affinity of the CH3 domains (3) to each other.
(1) scLIGHT-RBD; (2) CH2 domain; (3) CH3 domain; (4) Hinge-Cysteines (left side: oxidized to disulfide bridges; right side reduced stage with free thiols); (5) CH2-Carbohydrates attached to N297 position (EU-numbering); (6) Upper Hinge Lysine (K223).

CH2 (Heavy chain constant domain 2)-glycosylation present on the inner surface areas normally shields the subdomain from proteases during "open Fc-conformation transits" wherein hinge-interchain disulfide bonds are reduced and the covalent interchain linkage is disrupted (FIG. 5). This enables CH2-dissociation and exposure of the inner surface area towards proteases. LIGHT receptor agonist proteins comprising an Fc-domain with a N297S equivalent mutation of SEQ ID NO: 15 (PROTEIN A) (according to the EU numbering system) creates an aglycosylated-CH2 and are therefore likely to be subject to protease digestion and less stable than equivalent structures with wild-type CH2 glycosylation. This would impact the compound's stability during USP/DSP/storage, where host cell proteases are present and have long-term access to the structure. Accordingly, in certain embodiments, the LIGHT receptor agonist lacks CH2 glycosylation sites, but comprises glycosylation sites in the linker sequences of each polypeptide chain (e.g., GSGSGNGS, SEQ ID NO: 2).

According to a preferred embodiment of the invention, the antibody Fc fragment domain is fused via a hinge-linker element. The hinge-linker element has a length of 10-30 amino acids, particularly a length of 15-25 amino acids, e.g. 22 amino acids. The term "hinge-linker" includes any linker long enough to allow the domains attached by the hinge-linker element to attain a biologically active confirmation. The hinge-linker element preferably comprises the hinge-region sequence of an immunoglobulin, herein referred to as "Ig hinge-region". The term "Ig hinge-region" means any polypeptide comprising an amino acid sequence that shares sequence identity or similarity with a portion of a naturally occurring Ig hinge-region sequence which includes one or more cysteine residues, e.g., two cysteine residues, at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution.

The number of molecules with open Fc-conformation in an individual LIGHT receptor agonist protein depends on the number of interchain-disulfide bonds present in the hinge region. Accordingly, in one embodiment a third cysteine (C225 according to the EU numbering system) was introduced into the hinge region of the LIGHT receptor agonist proteins of the instant invention in order to ameliorate the effect of depleting the CH2-glycosites.

Exchange of a Lysine to Glycine in the Hinge Region Results in Enhanced Proteolytic Stability In one embodiment, the LIGHT receptor agonist proteins of the invention additionally comprise a mutation of the upper-hinge lysine (K223, according to the EU numbering system) to a glycine to reduce proteolytic processing at this site, thereby enhancing the overall stability of the fusion protein. Combining aforementioned introduction of a third cysteine (C225, according to the EU numbering system) with the aforementioned lysine to glycine mutation (K223G, according to the EU numbering system) within the hinge region results in an overall stabilized LIGHT receptor agonist protein of the instant invention.

A particularly preferred hinge-linker element including the aforementioned cysteine (C225) and the lysine to glycine mutation (K223G) comprises or consists of the amino acid sequence as shown in SEQ ID NO: 16 (Table 4).

The LIGHT receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 17 (Table 4).

Further, the LIGHT receptor agonist protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain. According to a preferred embodiment, the fusion polypeptide comprises a Strep-tag fused to the C-terminus via a short serine linker as shown in SEQ ID NO: 18 (Table 4).

Preferred hinge-linker elements (SEQ ID NO: 16, 19-24), a preferred N-terminal signal peptide domain (SEQ ID NO: 17) and serine linker-strep tag (SEQ ID NO: 18) are shown in Table 4.

TABLE 4

Exemplary domains and linkers

| SEQ ID NO | Sequence |
| --- | --- |
| 16 | GSSSSSSSSGSCDKTHTCPPC |
| 17 | METDTLLVFVLLVWVPAGNG |
| 18 | SSSSSSAWSHPQFEK |
| 19 | GSSSSSSSGSCDKTHTCPPC |

TABLE 4-continued

Exemplary domains and linkers

| SEQ ID NO | Sequence |
| --- | --- |
| 20 | GSSSSSSGSCDKTEITCPPC |
| 21 | GSSSSSGSCDKTHTCPPC |
| 22 | GSSSGSCDKTHTCPPC |
| 23 | GSSSGSCDKTHTCPPCGS |
| 24 | GSSSGSCDKTHTCPPCGSGS |

In one embodiment of the invention, the fusion polypeptide comprises three soluble LIGHT domains fused by two different peptide linker elements. The first linker element (ii) consists of SEQ ID NO: 2. The second linker element (iv) consists of SEQ ID NO: 11. The first soluble LIGHT domain (i) consists of amino acids 91-240 of human LIGHT according to SEQ ID NO: 1 and the soluble LIGHT domains (iii) and (v) consist of amino acids 94-240 of human LIGHT according to SEQ ID NO: 1. The resulting scLIGHT-RBD sequence module is shown in Table 5b SEQ ID NO: 36.

In another embodiment of the invention, the fusion polypeptide comprises three soluble LIGHT domains fused by peptide linker elements of SEQ ID NO: 2. The first soluble LIGHT domain (i) consists of amino acids 91-240 of human LIGHT according to SEQ ID NO: 1 and the soluble LIGHT domains (iii) and (v) consist of amino acids 93-240 of human LIGHT according to SEQ ID NO: 1. The resulting scLIGHT-RBD sequence module is shown in table 5b SEQ ID NO: 39.

In another embodiment of the invention, the fusion polypeptide comprises three soluble LIGHT domains fused by peptide linker elements of SEQ ID NO: 2. The first soluble LIGHT domain (i) consists of amino acids 91-240 of human LIGHT according to SEQ ID NO: 1 and the soluble LIGHT domains (iii) and (v) consist of amino acids 94-240 of human LIGHT according to SEQ ID NO: 1. The resulting scLIGHT-RBD sequence module is shown in table 5b SEQ ID NO: 40.

Preferred Configuration LIGHT-Fc

Additionally, the fusion polypeptide comprises an antibody Fc fragment domain according to SEQ ID NO: 13 that is fused C-terminally to the soluble LIGHT domain (v) via a hinge-linker according to SEQ ID NO: 16. The inventors surprisingly found that this particular fusion polypeptide provides improved biological activity as compared to bivalent agonistic anti-LIGHT-receptor-mAB and has a prolonged stability as compared to similar fusion proteins comprising a lysine in position 223 and a N297S mutation in the CH2 domain (according to the EU numbering). The amino acid sequence of an exemplary embodiment of a LIGHT receptor agonist protein of the invention is set forth in SEQ ID NO: 27.

Further, the fusion polypeptide may comprise an N-terminal signal peptide domain e.g. according to SEQ ID NO: 17. A specific example of a LIGHT receptor agonist protein of the invention is shown in SEQ ID NO: 25.

According to another preferred embodiment, the fusion polypeptide may additionally comprise a C-terminal Strep-tag that is fused to the polypeptide of the invention via a short serine linker as shown in SEQ ID NO: 18. According to this aspect of the invention, the Fc fragment preferably consists of the amino acid sequence as shown in SEQ ID NO: 13 or 14.

Further, the Fc fragment may consist of a shorter Fc fragment, for example including amino acids 1-217 of SEQ ID NO: 13. Particularly preferred examples of fusion polypeptides comprising a C-terminal Strep-tag are shown in SEQ ID NO: 15 (PROTEIN A).

The exemplary LIGHT receptor agonist proteins as shown in SEQ ID Nos: 15, 25, and 26, each comprises an N-terminal signal peptide domain, at amino acids 1-20 of each sequence. In each case, the mature protein starts with amino acid 21. Mature exemplary LIGHT receptor agonist proteins (without a signal peptide) of the instant invention are set forth in SEQ ID NO: 27-35.

Exemplary LIGHT receptor agonist proteins described above are shown in Table 5.

The LIGHT receptor agonist as set forth in SEQ ID NO: 27 has a reduced total number of glycosylation sites (the N297S mutation in the CH2 region providing an aglycosylated CH2 domain, according to the EU numbering system), an increased number of interchain disulfide bonds in the hinge region, and the mutation of an upper-hinge lysine to a glycine (K223G, according to the EU numbering system). Additional, the second peptide linker (iv) is shortened and the modules (iii) and (v) are N-terminal shortened, thereby reducing all in all protomer dissociation and enhancing the proteins stability towards proteases These alterations provide a decrease in potential degradation and LIGHT receptor superclustering (along with concomitant toxicity).

The LIGHT receptor agonist as set forth in SEQ ID NO: 30 comprises the same layout as SEQ ID NO: 27 but with the E91Q mutation in the soluble LIGHT domains (i) thereby enabling formation of pyroglutamate leading to protection of the N-terminus against aminopeptidases and subsequently enhancing the overall stability of the protein during manufacture and storage.

The LIGHT receptor agonist as set forth in SEQ ID NO: 32 comprises the same layout as SEQ ID NO: 30 but with the third peptide linker (vi) shortened to reduce the interdomain distance between the soluble LIGHT domain (v) and the Fc-domain (Vii) thereby enhancing the proteins stability towards proteases.

According to one embodiment of the invention, the single-chain LIGHT fusion polypeptide domain comprises a scLIGHT-RBD module as shown in SEQ ID NO: 39 optionally with the soluble domain (i) comprising the E91Q mutation. A specific example of a LIGHT receptor agonist protein of the invention comprising the E91Q mutein in domain (i), the hinge linker of SEQ ID NO: 16 and an antibody Fc fragment according to SEQ ID NO: 13 is shown in SEQ ID NO: 30.

TABLE 5

Exemplary LIGHT receptor agonist Proteins

| SEQ ID NO | Sequence |
| --- | --- |
| 25<br>PROTEIN A<br>without Strep | METDTLLVFVLLVWVPAGNGEVNPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMVGSGS |

TABLE 5-continued

Exempary LIGHT receptor agonist Proteins

| SEQ ID NO | Sequence |
|---|---|
| | GNGSPAAHLTGANSSLTGSGGPLLWETQLGLAFLRGLSYHDGALVVTKAGYYYIYSKV<br>QLGGVGCPLGLASTITHGLYKRTPRYPEELELLVSQQSPCGRATSSSRVWWDSSFLGG<br>VVHLEAGEEVVVRVLDERLVRLRDGTRSYFGAFMVGSGSPAAHLTGANSSLTGSGGPL<br>LWETQLGLAFLRGLSYHDGALVVTKAGYYYIYSKVQLGGVGCPLGLASTITHGLYKRT<br>PRYPEELELLVSQQSPCGRATSSSRVWWDSSFLGGVVHLEAGEEVVVRVLDERLVRLR<br>DGTRSYFGAFMVGSSSSSSSGSCDKTHTCPPCPAPELLGGPSVFLFPPKPKDTLMIS<br>RTPEVTCVVVDVSHEDPEVKFNWYVDGVEVHNAKTKPREEQ<u>Y</u>SSTYRVVSVLTVLHQD<br>WLNGKEYKCKVSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRWQQGNVFSCSVM<br>HEALHNHYTQKSLSLSPGK |
| 15<br>PROTEIN A<br>SEQ36 +<br>SEQ13 (FC) +<br>Signal +<br>Strap | METDTLLVFVLLVWVPAGNGEVNPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMVGSGS<br>GNGSPAAHLTGANSSLTGSGGPLLWETQLGLAFLRGLSYHDGALVVTKAGYYYIYSKV<br>QLGGVGCPLGLASTITHGLYKRTPRYPEELELLVSQQSPCGRATSSSRVWWDSSFLGG<br>VVHLEAGEEVVVRVLDERLVRLRDGTRSYFGAFMVGSGSPAAHLTGANSSLTGSGGPL<br>LWETQLGLAFLRGLSYHDGALVVTKAGYYYIYSKVQLGGVGCPLGLASTITHGLYKRT<br>PRYPEELELLVSQQSPCGRATSSSRVWWDSSFLGGVVHLEAGEEVVVRVLDERLVRLR<br>DGTRSYFGAFMVGSSSSSSSGSCDKTHTCPPCPAPELLGGPSVFLFPPKPKDTLMIS<br>RTPEVTCVVVDVSHEDPEVKFNWYVDGVEVHNAKTKPREEQ<u>Y</u>SSTYRVVSVLTVLHQD<br>WLNGKEYKCKVSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRWQQGNVFSCSVM<br>HEALHNHYTQKSLSLSPGSSSSSSSAWSHPQFEK |
| 26<br>SEQ36 +<br>SEQ14 (FC) +<br>Signal<br>No Strap | METDTLLVFVLLVWVPAGNGEVNPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMVGSGS<br>GNGSPAAHLTGANSSLTGSGGPLLWETQLGLAFLRGLSYHDGALVVTKAGYYYIYSKV<br>QLGGVGCPLGLASTITHGLYKRTPRYPEELELLVSQQSPCGRATSSSRVWWDSSFLGG<br>VVHLEAGEEVVVRVLDERLVRLRDGTRSYFGAFMVGSGSPAAHLTGANSSLTGSGGPL<br>LWETQLGLAFLRGLSYHDGALVVTKAGYYYIYSKVQLGGVGCPLGLASTITHGLYKRT<br>PRYPEELELLVSQQSPCGRATSSSRVWWDSSFLGGVVHLEAGEEVVVRVLDERLVRLR<br>DGTRSYFGAFMVGSSSSSSSSGSCDKTHTCPPCPAPPVAGPSVFLFPPKPKDTLMISR<br>TPEVTCVVVDVSHEDPEVKFNWYVDGVEVHNAKTKPREEQY<u>N</u>STYRVVSVLTVLHQDW<br>LNGKEYKCKVSNKGLPSSIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMH<br>EALHNHYTQKSLSLSPGK |
| 27<br>SEQ36 +<br>SEQ13 (FC)<br>No Signal<br>No Strap<br>No Glyco | EVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSGG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSPAAHLTGANSSLTGSGGPLLWETQLGLAFLRGLSYHDGA<br>LVVTKAGYYYIYSKVQLGGVGCPLGLASTITHGLYKRTPRYPEELELLVSQQSPCGRA<br>TSSSRVWWDSSFLGGVVHLEAGEEVVVRVLDERLVRLRDGTRSYFGAFMVGSSSSSSS<br>SGSCDKTHTCPPCPAPELLGGPSVFLFPPKPKDTLMISRTPEVTCVVVDVSHEDPEVK<br>FNWYVDGVEVHNAKTKPREEQYSSTYRVVSVLTVLHQDWLNGKEYKCKVSNKALPAPI<br>EKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQKSLSLSPGK |
| 28<br>SEQ36 +<br>SEQ13 (FC)<br>No Signal +<br>StrepTag<br>No Glyco | <u>E</u>VNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSPAAHLTGANSSLTGSGGPLLWETQLGLAFLRGLSYHDGA<br>LVVTKAGYYYIYSKVQLGGVGCPLGLASTITHGLYKRTPRYPEELELLVSQQSPCGRA<br>TSSSRVWWDSSFLGGVVHLEAGEEVVVRVLDERLVRLRDGTRSYFGAFMVGSSSSSSS<br>SGSCDKTHTCPPCPAPELLGGPSVFLFPPKPKDTLMISRTPEVTCVVVDVSHEDPEVK<br>FNWYVDGVEVHNAKTKPREEQY<u>S</u>STYRVVSVLTVLHQDWLNGKEYKCKVSNKALPAPI<br>EKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQKSLSLSPGSS<br>SSSSAWSHPQFEK |
| 29<br>SEQ36 +<br>SEQ14 (FC)<br>No Signal<br>No strep<br>Glyco FC | EVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSPAAHLTGANSSLTGSGGPLLWETQLGLAFLRGLSYHDGA<br>LVVTKAGYYYIYSKVQLGGVGCPLGLASTITHGLYKRTPRYPEELELLVSQQSPCGRA<br>TSSSRVWWDSSFLGGVVHLEAGEEVVVRVLDERLVRLRDGTRSYFGAFMVGSSSSSSS<br>SGSCDKTHTCPPCPAPPVAGPSVFLFPPKPKDTLMISRTPEVTCVVVDVSHEDPEVKF<br>NWYVDGVEVHNAKTKPREEQY<u>N</u>STYRVVSVLTVLHQDWLNGKEYKCKVSNKGLPSSIE |

TABLE 5-continued

Exempary LIGHT receptor agonist Proteins

| SEQ ID NO | Sequence |
|---|---|
| | KTISKAKGQPREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKSLSLSPGK |
| 30<br>Same as 27<br>with E91Q in | QVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSPAAHLTGANSSLTGSGGPLLWETQLGLAFLRGLSYHDGA<br>LVVTKAGYYYIYSKVQLGGVGCPLGLASTITHGLYKRTPRYPEELELLVSQQSPCGRA<br>TSSSRVWWDSSFLGGVVHLEAGEEVVVRVLDERLVRLRDGTRSYFGAFMVGSSSSSSS<br>SGSCDKTHTCPPCPAPELLGGPSVFLFPPKPKDTLMISRTPEVTCVVVDVSHEDPEVK<br>FNWYVDGVEVHNAKTKPREEQYSSTYRVVSVLTVLHQDWLNGKEYKCKVSNKALPAPI<br>EKTISKAKGQPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQKSLSLSPGK |
| 31<br>Protein B<br>SEQ 39<br>With L1 8 mer<br>L2: 8 mer | QVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSNPAAHLTGANSSLTGS<br>GGPLLWETQLGLAFLRGLSYHDGALVVTKAGYYYIYSKVQLGGVGCPLGLASTITHGL<br>YKRTPRYPEELELLVSQQSPCGRATSSSRVWWDSSFLGGVVHLEAGEEVVVRVLDERL<br>VRLRDGTRSYFGAFMVGSGSGNGSNPAAHLTGANSSLTGSGGPLLWETQLGLAFLRGL<br>SYHDGALVVTKAGYYYIYSKVQLGGVGCPLGLASTITHGLYKRTPRYPEELELLVSQQ<br>SPCGRATSSSRVWWDSSFLGGVVHLEAGEEVVVRVLDERLVRLRDGTRSYFGAFMVGS<br>SSSSSSSGSCDKTHTCPPCPAPELLGGPSVFLFPPKPKDTLMISRTPEVTCVVVDVSH<br>EDPEVKFNWYVDGVEVHNAKTKPREEQYSSTYRVVSVLTVLHQDWLNGKEYKCKVSNK<br>ALPAPIEKTISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHNHYTQKSLS<br>LSPGK |
| 32<br>Same as 30,<br>shortened<br>hinge | QVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSPAAHLTGANSSLTGSGGPLLWETQLGLAFLRGLSYHDGA<br>LVVTKAGYYYIYSKVQLGGVGCPLGLASTITHGLYKRTPRYPEELELLVSQQSPCGRA<br>TSSSRVWWDSSFLGGVVHLEAGEEVVVRVLDERLVRLRDGTRSYFGAFMVgsssssgs<br>CDKTHTCPPCPAPELLGGPSVFLFPPKPKDTLMISRTPEVTCVVVDVSHEDPEVKFNW<br>YVDGVEVHNAKTKPREEQYSSTYRVVSVLTVLHQDWLNGKEYKCKVSNKALPAPIEKT<br>ISKAKGQPREPQVYTLPPSREEMTKNQVSLTCLVKGFYPSDIAVEWESNGQPENNYKT<br>TPPVLDSDGSFFLYSKLTVDKSRWQQGNVFSCSVMHEALHNHYTQKSLSLSPGK |
| 33<br>Linker1 + 2<br>8 mer<br>N93-deletionin<br>RBD module 2<br>and 3 | EVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSS<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSGNGSPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMVGSSS<br>SSSSSGSCDKTHTCPPCPAPELLGGPSVFLFPPKPKDTLMISRTPEVTCVVVDVSHED<br>PEVKFNWYVDGVEVHNAKTKPREEQYSSTYRVVSVLTVLHQDWLNGKEYKCKVSNKAL<br>PAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLS<br>PGK |
| 34<br>SEQ33 with<br>N-terminal<br>amino acid<br>exchange<br>E → Q | QVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSGNGSPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMVGSSS<br>SSSSSGSCDKTHTCPPCPAPELLGGPSVFLFPPKPKDTLMISRTPEVTCVVVDVSHED<br>PEVKFNWYVDGVEVHNAKTKPREEQYSSTYRVVSVLTVLHQDWLNGKEYKCKVSNKAL<br>PAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLS<br>PGK |
| 35<br>Seq33 with<br>shorter<br>hinge-linker | EVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV |

TABLE 5-continued

Exempary LIGHT receptor agonist Proteins

| SEQ ID NO | Sequence |
|---|---|
| | RLRDGTRSYFGAFMVGSGSGNGSPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMVgsss<br>ssgsCDKTHTCPPCPAPELLGGPSVFLFPPKPKDTLMISRTPEVTCVVVDVSHEDPEV<br>KFNWYVDGVEVHNAKTKPREEQYsstYRVVSVLTVLHQDWLNGKEYKCKVSNKALPAP<br>IEKTISKAKGQPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYTQKSLSLSPGK |

TABLE 5B

Exemplary scLIGHT-RBD modules

| 36<br>L1 8 mer<br>L2 4 mer | EVNPAAHLTGANSSLTGSGGPLLWETQLGLAFLRGLSYHDGALVVTKAGYYYI<br>YSKVQLGGVGCPLGLASTITHGLYKRTPRYPEELELLVSQQSPCGRATSSSRV<br>WWDSSFLGGVVHLEAGEEVVVRVLDERLVRLRDGTRSYFGAFMVGSGSGNGSP<br>AAHLTGANSSLTGSGGPLLWETQLGLAFLRGLSYHDGALVVTKAGYYYIYSKV<br>QLGGVGCPLGLASTITHGLYKRTPRYPEELELLVSQQSPCGRATSSSRVWWDS<br>SFLGGVVHLEAGEEVVVRVLDERLVRLRDGTRSYFGAFMVGSGSPAAHLTGAN<br>SSLTGSGGPLLWETQLGLAFLRGLSYHDGALVVTKAGYYYIYSKVQLGGVGCP<br>LGLASTITHGLYKRTPRYPEELELLVSQQSPCGRATSSSRVWWDSSFLGGVVH<br>LEAGEEVVVRVLDERLVRLRDGTRSYFGAFMV |
|---|---|
| 39<br>L1 8 mer<br>L2 8 mer | EVNPAAHLTGANSSLTGSGGPLLWETQLGLAFLRGLSYHDGALVVTKAGYYYI<br>YSKVQLGGVGCPLGLASTITHGLYKRTPRYPEELELLVSQQSPCGRATSSSRV<br>WWDSSFLGGVVHLEAGEEVVVRVLDERLVRLRDGTRSYFGAFMVGSGSGNGSN<br>PAAHLTGANSSLTGSGGPLLWETQLGLAFLRGLSYHDGALVVTKAGYYYIYSK<br>VQLGGVGCPLGLASTITHGLYKRTPRYPEELELLVSQQSPCGRATSSSRVWWD<br>SSFLGGVVHLEAGEEVVVRVLDERLVRLRDGTRSYFGAFMVGSGSGNGSNPAA<br>HLTGANSSLTGSGGPLLWETQLGLAFLRGLSYHDGALVVTKAGYYYIYSKVQL<br>GGVGCPLGLASTITHGLYKRTPRYPEELELLVSQQSPCGRATSSSRVWWDSSF<br>LGGVVHLEAGEEVVVRVLDERLVRLRDGTRSYFGAFMV |
| 40<br>L1 8 mer<br>L2 8 mer<br>N93 Deleted<br>mod-2 and 3 | EVNPAAHLTGANSSLTGSGGPLLWETQLGLAFLRGLSYHDGALVVTKAGYYYIYSKVQ<br>LGGVGCPLGLASTITHGLYKRTPRYPEELELLVSQQSPCGRATSSSRVWWDSSFLGGV<br>VHLEAGEEVVVRVLDERLVRLRDGTRSYFGAFMVGSGSGNGSPAAHLTGANSSLTGSG<br>GPLLWETQLGLAFLRGLSYHDGALVVTKAGYYYIYSKVQLGGVGCPLGLASTITHGLY<br>KRTPRYPEELELLVSQQSPCGRATSSSRVWWDSSFLGGVVHLEAGEEVVVRVLDERLV<br>RLRDGTRSYFGAFMVGSGSGNGSPAAHLTGANSSLTGSGGPLLWETQLGLAFLRGLSY<br>HDGALVVTKAGYYYIYSKVQLGGVGCPLGLASTITHGLYKRTPRYPEELELLVSQQSP<br>CGRATSSSRVWWDSSFLGGVVHLEAGEEVVVRVLDERLVRLRDGTRSYFGAFMV |

Furthermore, it has to be noted that the scLIGHT-RBD modules (SEQ ID NO: 36, 39 and SEQ ID NO: 40) are well suited to generate fusion proteins with additional domains fused to either N- or C-terminal end employing the linkers described in Table 2 (SEQ ID NO: 2-12).

Above presented embodiments of the LIGHT receptor agonist proteins of the invention either address stability influencing construction principles or aggregation resistance of soluble receptor agonist proteins of the invention or modulate receptor binding and activity of the receptor agonist proteins.

A further important property for describing suitability of a substance as an active agent in medical preparations is its pharmacokinetic profile (PK profile) Pharmacokinetics is the study of drug disposition in the body and focuses on the changes in drug plasma concentration. For any given drug and dose, the plasma concentration will vary depending on the processes of absorption, distribution and elimination. The time dependent decline of plasma drug concentration and its final elimination from the body mainly depends on biotransformation and excretion of the drug and is generally measured as in vivo half-life time (Pharmacology, 4th Edition; Elesevier 2013).

Understanding the course of events that make up the immune response against a pathogen or a tumor allows to determine advantageous PK profiles of the LIGHT receptor agonist proteins of the invention. The immune response against a pathogen or indeed a tumor carrying antigens can be divided into several phases. Each phase shows a characteristic duration and events usually take place in specialized tissues. In particular, the priming phase describes early events in an immune response when lymphocytes are being presented with tumor-associated antigens in secondary lymphoid organs. In order to recognize antigens through their T cell or B cell receptor, T cells and B cells, respectively, need to form cell-cell conjugates with antigen-presenting cells (APC). In case of successful antigen-recognition, lymphocytes are also being presented with co-stimulatory molecules such as LIGHT by the APC. As both presentation of antigen and co-stimulatory molecules occurs at the interface of the APC/lymphocyte conjugate, this interaction is rather short lived as the conjugate falls apart after several minutes or very few hours. Following antigen recognition and co-stimulation with molecules such as LIGHT lymphocytes become activated and enter the expansion phase during which they proliferate in order to mount an immune response against the tumor.

In light of the short physical interaction of APCs and lymphocytes in secondary lymphoid organs, one could speculate that the co-stimulatory signal elicited by recombinant biologics targeting the LIGHT-RECEPTOR pathway is desired to be short-lived. In fact, long exposition to co-stimulatory signals might push lymphocytes into a hyper-activated state possibly leading to systemic toxic effects. Consequently, a favorable PK profile for biologics targeting co-stimulatory pathways of the immune system would show a comparably short terminal half-life in the range of hours or possibly one day. This would be in contrast to antibodies targeting the same pathways, which usually show a terminal half-life of multiple days or even more than one week. In summary, biologics activating co-stimulatory pathways of the immune system having a half-life in the range of several hours are closer to the natural ligand in term of their temporal activity in comparison to stimulating antibodies. This could also make a positive contribution to possible toxicity effects observed during the treatment with some immune-stimulating antibodies. Thus, in a further embodiment, the LIGHT receptor agonist proteins of the invention have a short terminal half live such as less than 4 days, less than three days, less than two days, less than one day.

A further aspect of the present invention relates to a nucleic acid molecule encoding a LIGHT receptor agonist protein as described herein. The nucleic acid molecule may be a DNA molecule, e.g. a double-stranded or single-stranded DNA molecule, or an RNA molecule. The nucleic acid molecule may encode the LIGHT receptor agonist protein or a precursor thereof, e.g. a pro- or pre-proform of the LIGHT receptor agonist protein which may comprise a signal sequence or other heterologous amino acid portions for secretion or purification which are preferably located at the N- and/or C-terminus of the LIGHT receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 37. This nucleic acid molecule comprises the open reading frame encoding the fusion polypeptide of SEQ ID NO: 25.

TABLE 6

Nucleic Add Sequence of Exemplary LIGHT receptor agonist Protein

| SEQ ID NO | Sequence |
|---|---|
| 37 | AAGCTTTAGGGATAACAGGGTAATAGCCGCCACCATGGAGACTGACACCCTGCTGG TGTTCGTGCTGCTGGTCTGGGTGCCTGCAGGAAATGGAGAAGTGAACCCCGCCGCC CATCTGACCGGCGCTAACAGCAGCCTGACAGGTTCTGGCGGACCCCTCCTGTGGGA GACACAACTGGGCCTGGCCTTCCTGAGGGGCCTGAGCTACCATGATGGCGCCCTGG TGGTGACCAAGGCCGGCTACTACTACATCTATTCCAAGGTCCAGCTCGGAGGCGTG GGATGCCCTCTGGGACTGGCCTCCACCATCACCCACGGCCTGTACAAGCGGACCCC TAGGTACCCCGAGGAACTGGAACTGCTCGTCTCCAACAGAGCCCTTGCGGCAGGG CTACCTCCTCCAGCAGGGTGTGGTGGGACTCCAGCTTCCTGGGAGGCGTCGTCCAC CTGGAGGCTGGAGAAGAAGTGGTGGTGCGGGTCCTGGACGAAAGGCTGGTGAGGCT CAGGGACGGCACCCGGTCCTACTTTGGAGCCTTTATGGTGGGCTCCGGATCTGGTA ACGGCAGCCCCGCTGCTCATCTGACAGGCGCCAATAGCAGCCTGACAGGCAGCGGA GGCCCTCTGCTGTGGGAAACACAGCTGGGCCTGGCCTTTCTGAGGGGCCTGTCCTA TCACGATGGAGCCCTGGTGGTGACCAAAGCCGGCTATTACTATATCTACAGCAAGG TGCAGCTGGGCGGAGTGGGATGTCCTCTGGGCCTGGCCTCCACCATCACACACGGA CTGTATAAGCGGACACCTAGGTATCCCGAAGAGCTGGAGCTCCTGGTGTCCCAGCA AAGCCCTTGTGGAAGGGCTACCTCCAGCAGCAGGGTCTGGTGGGACTCCTCCTTCC TGGGCGGCGTGGTCCATCTGGAAGCTGGCGAGGAGGTGGTGGTGAGGGTCCTGGAT GAGAGGCTGGTCAGGCTGAGGGATGGCACCCGGTCCTATTTTGGCGCTTTCATGGT GGGCTCTGGTAGCCCTGCCGCCCACCTGACAGGAGCCAACAGCAGCCTGACAGGAA GCGGCGGCCCTCTGCTGTGGGAGACCCAACTGGGCCTGGCCTTCCTGCGGGGCCTC TCCTACCACGACGGCGCTCTGGTGGTGACCAAGGCCGGCTATTATTATATCTACTC CAAAGTCCAGCTGGGAGGCGTCGGCTGTCCTCTCGGACTGGCTTCCACCATCACCC ATGGCCTGTACAAAAGGACCCCTAGGTACCCCGAAGAGTTAGAACTGCTGGTCTCC CAGCAGTCCCCTTGCGGAAGGGCCACAAGCAGCAGCCGGGTGTGGTGGGACTCCPG CTTTCTGGGCGGAGTGGTGCACCTGGAAGCCGGAGAGGAGGTCGTGGTCAGGGTCC TGGATGAAAGGCTGGTGCGGCTGAGGGATGGCACCAGGTCCTATTTCGGCGCCTTC ATGGTCggatcctcgagTTCATCGTCCTCATCCGGCTCATGTGATAAGACCCACAC CTGCCCTCCCTGTCCTGCCCCTGAGCTGCTGGGCGGACCTTCTGTGTTCCTGTTCC CCCCCAAGCCTAAGGACACCCTGATGATCTCCAGGACCCCTGAGGTGACCTGTGTG GTGGTGGACGTGTCTCACGAAGATCCCGAGGTGAAGTTCAACTGGTACGTGGACGG CGTGGAGGTCCACAACGCCAAGACCAAGCCTAGGGAGGAGCAGTACAGCTCCACCT ACCGGGTGGTGTCTGTGCTGACCGTGCTGCACCAGGATTGGCTGAACGGAAAGGAG TATAAGTGTAAGGTCTCCAACAAGGCCCTGCCTGCCCCCATCGAGAAAACCATCTC CAAGGCCAAGGGCCAGCCTCGGGAGCCTCAGGTGTACACCCTGCCTCCTAGCAGGG AGGAGATGACCAAGAACCAGGTGTCCCTGACCTGTCTGGTGAAGGGCTTCTACCCT TCCGATATCGCCGTGGAGTGGGAGTCTAATGGCCAGCCCGAGAACAACTACAAGAC CACCCCTCCTGTGCTGGACTCTGACGGCTCCTTCTTCCTGTACTCCAAGCTGACCG TGGACAAGTCCAGATGGCAGCAGGGCAACGTGTTCTCCTGCTCCGTGATGCACGAG GCCCTGCACAATCACTACACCCAGAAGTCCCTGTCTCTGAGTCCGGGCAAGTAATA ggcgcgcc |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc. Examples of suitable expression control sequences and vectors are described for example by Sambrook et al. (1989) Molecular Cloning, A Laboratory Manual, Cold Spring Harbor Press, and Ausubel et al. (1989), Current Protocols in Molecular Biology, John Wiley & Sons or more recent editions thereof.

Various expression vector/host cell systems may be used to express the nucleic acid sequences encoding the LIGHT receptor agonist proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one LIGHT receptor agonist protein, a respective nucleic acid encoding therefore, or a transformed or transfected cell, all as described herein.

In another aspect, the present invention provides a pharmaceutical composition comprising a LIGHT receptor agonist protein disclosed herein and one or more pharmaceutically acceptable carriers, diluents, excipients, and/or adjuvants. In another aspect, the present invention provides a nucleic acid molecule encoding the LIGHT receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NS0, CRL7030, HsS78Bst, PER.C6, SP2/0-Agl4, and hybridoma cells.

In another aspect, the present invention provides a method of treating a subject having a LIGHT-associated disease or disorder, the method comprising administering to the subject an effective amount of the LIGHT receptor agonist protein. In one embodiment, the LIGHT receptor agonist protein is administered alone. In another embodiment, the LIGHT receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma. In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors.

In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax. In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the LIGHT receptor agonist protein is administered as a single bolus. In another embodiment, LIGHT receptor agonist protein may be administered over several divided doses. The LIGHT receptor agonist protein can be administered at about 0.1-100 mg/kg. In one embodiment, the LIGHT receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, and 10-100 mg/kg. In other embodiments, the LIGHT receptor agonist protein is present in pharmaceutical compositions at about 0.1-100 mg/ml. In one embodiment, the LIGHT receptor agonist protein is present in pharmaceutical compositions at an amount selected from the group consisting of: about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of LIGHT receptor agonist protein is administered to a subject. In another embodiment, a prophylactically effective amount of LIGHT receptor agonist protein is administered to a subject.

The term "LIGHT-associated disease or disorder" as used herein is any disease or disorder which may be ameliorated by administering an effective amount of a LIGHT receptor agonist to a subject in need thereof. At least one LIGHT receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of LIGHT, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of LIGHT" as used herein is to be understood as any function or expression of LIGHT that deviates from the normal function or expression of LIGHT, e.g., overexpression of the LIGHT gene or protein, reduced or abolished expression of the LIGHT gene or protein compared to the normal physiological expression level of LIGHT, increased activity of LIGHT, reduced or abolished activity of LIGHT, increased binding of LIGHT to any binding partners, e.g., to a receptor, particularly a LIGHT receptor or another cytokine molecule, reduced or abolished binding to any binding partner, e.g. to a receptor, particularly a LIGHT receptor or another cytokine molecule, compared to the normal physiological activity or binding of LIGHT.

In various embodiments, a method is provided for treating a human subject suffering from a disorder which can be treated by targeting LIGHT-receptors comprising administering to the human subject a LIGHT receptor agonist protein disclosed herein such that the effect on the activity of the target, or targets, in the human subject is agonistic, one or more symptoms is alleviated, and/or treatment is achieved. The LIGHT receptor agonist proteins provided herein can be used to treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a LIGHT receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-HVEM, anti-BTLA, LIGHT fusion protein, anti-CD137, anti-CD137L, anti-OX40, anti-OX40L, anti-CD70, anti-CD27, anti-GAL9, anti-A2AR, anti-KIR, anti-IDO-1, anti-CD20), a dendritic cell/antigen-presenting cell modulator (including but not limited to anti-CD40 antibody, anti-CD40L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the LIGHT receptor agonist protein(s) can be used alone or in combination with one or more additional agents, e.g., a chemotherapeutic, radiotherapy, or biological agent. In some embodiments, the agent can include the following: 13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron® Anastrozole; Arabinosylcytosine; Ara-C Aranesp®; Aredia®; Arimidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar® Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Duvelisib; Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol Etopophos®; Etoposide; Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; ipilimumab, Iressa®; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Lirilumab; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®, Medrol®; Megace®, Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Nivolumab; Novantrone® Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pembrolizumab; Pentostatin; Pertuzumab; Phenylalanine Mustard; Pidilizumab; Platinol®; Platinol-AQ®; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Corteft Solu-Medrol®; Sorafenib; SPRYCEL™; STI-571; STIVAGRA, Streptozocin; SU11248; Sunitinib; Sutent®; Tamoxifen Tarceva®; Targretin®; Tasigna®; Taxol®; Taxotere®; Temodar®, Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadurm; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalinm; Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more LIGHT receptor agonist proteins, either alone or in combination with prophylactic agents, therapeutic agents, and/or pharmaceutically acceptable carriers are provided herein. In various embodiments, nonlimiting examples of the uses of the pharmaceutical compositions disclosed herein include diagnosing, detecting, and/or monitoring a disorder, preventing, treating, managing, and/ or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

As used herein, the phrase "effective amount" means an amount of LIGHT agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of LIGHT or with a LIGHT-associated disease or disorder.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a LIGHT receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the LIGHT receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES

Example 1

Manufacture of a LIGHT Receptor Agonist Protein

A) Amino Acids Met1-Gly20
 Ig-Kappa-signal peptide, assumed signal peptidase cleavage site after amino acid Gly 20.
B) Amino Acids Glu21-Val170
 First soluble cytokine domain of the human LIGHT (LIGHT, amino acid 91-240 of SEQ ID NO: 1).
C) Amino Acids Gly171-Ser 178
 First peptide linker element of SEQ ID NO: 2.
D) Amino Acids Pro179-Val325
 Second soluble cytokine domain of the human LIGHT (LIGHT, amino acid 94-240 of SEQ ID NO: 1).
E) Amino Acids Gly326-Ser329.
 Second peptide linker element of SEQ ID NO: 11.
F) Amino Acids Pro330-Val476
 Third soluble cytokine domain of the human LIGHT ligand (LIGHT, amino acid 94-240 of SEQ ID NO: 1).
G) Amino Acids Gly477-Cys497
 Hinge-linker element of SEQ ID NO: 16.
H) Amino Acids Pro498-Lys715
 Antibody Fc fragment domain of SEQ ID NO: 13.

The above LIGHT receptor agonist protein is shown in SEQ ID NO: 25

The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19-24.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 37.

Example 2

Expression and Purification 2.1 Cloning, Expression and Purification of Fusion Polypeptides The aforementioned fusion proteins are expressed recombinantly in two different eukaryotic host cells employing the methods described below:

Method for Small Scale Expression of Light Receptor Agonist Fusion Proteins:

For initial analysis of aforementioned LIGHT receptor agonist fusion proteins, Hek293 cells grown in DMEM+ GlutaMAX (GibCo) supplemented with 10% FBS, 100 units/ml Penicillin and 100 [mu]g/ml Streptomycin are transiently transfected with a plasmid containing an expression cassette for a fusion polypeptide and an appropriate selection marker, e.g. a functional expression cassette comprising a blasticidine, puromycin or hygromycin resistance gene. In those cases, where a plurality of polypeptide chains is necessary to achieve the final product, the expression cassettes will be either combined on one plasmid or positioned on different plasmids during the transfection. Cell culture supernatant containing recombinant fusion polypeptide will be harvested three days post transfection and clarified by centrifugation at 300×g followed by filtration through a 0.22 μm sterile filter.

Method for Large Scale Expression and Purification of LIGHT Receptor Agonist Fusion Proteins For larger scale expression of LIGHT receptor agonist fusion proteins to be used in vivo, synthetic DNA cassettes encoding the aforementioned proteins is inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors are introduced by electroporation into suspension adapted Chinese Hamster Ovary cells (CHO-S, Invitrogen). Appropriate selection pressure will be applied three days post-transfection to the transfected cells. Surviving cells carrying the vector derived resistance gene(s) are recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants are analyzed by ELISA-assays detecting the aforementioned proteins and the cell pools with the highest specific productivity which were expanded in shake flasks prior to protein production (orbital shaker, 100 rpm, shaking throw 50 mm).

For lab-scale protein production, individual cell pools are cultured for 7-12 days in chemically defined medium (PowerCHO2-CD, Lonza) at 37° C. and 7% CO2 atmosphere in a Wave bioreactor 20/50 EHT (GE-Healthcare). The basal medium is PowerCHO2-CD supplemented with 4 mM Glutamax. Wave culture is started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture is fed twice with PowerFeed A (Lonza), usually on day 2 (20% feed) and day 5 (30% feed). After the second feed, shaking frequency is increased to 22 rpm, as well as the shaking ankle to 8°.

The bioreactor is usually harvested in between day 7 to day 12 when the cell viability drops below 80%. First, the culture supernatant is clarified using a manual depth filtration system (Millipore Millistak Pod, MCOHC 0.054 m$^2$). For Strep-tagged proteins, Avidin is added to a final concentration of 0.5 mg/L. Finally, the culture supernatant containing the LIGHT receptor agonist fusion protein is sterile filtered using a bottle top filter (0.22 μm, PES, Corning) and stored at 2-8° C. until further processing.

For affinity purification Streptactin Sepharose is packed to a column (gel bed 2 ml), equilibrated with 15 ml buffer W (100 mM Tris-HCl, 150 mM NaCl, pH 8.0) or PBS pH 7.4 and the cell culture supernatant is applied to the column with a flow rate of approx. 4 ml/min. Subsequently, the column is washed with 15 ml buffer W and bound polypeptide is eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternative to the Streptactin Sepharose based method, the affinity purification is performed employing a column with immobilized Protein-A as affinity ligand and an Äkta chromatography system (GE-Healthcare). A solid phase material with high affinity for the FC-domain of the fusion protein was chosen: MABSelect Sure™ (GE Healthcare). Briefly, the clarified cell culture supernatant is loaded on a HiTrap MabSelectSure column (CV=5 ml) equilibrated in wash-buffer-1 (20 mM Pi, 95 mM NaCl, pH7.2) not exceeding a load of 10 mg fusion protein per ml column-bed. The column is washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column is then eluted with elution buffer (20 mM Pi, 95 mM NaCl, pH 3.5) and the eluate is collected in up to ten fractions with each fraction having a volume equal to column-bed volume (5 ml). Each fraction is neutralized with an equal volume of aforementioned wash-buffer-2. The linear velocity is set to 150 cm/h and kept constant during the aforementioned affinity chromatography method. The protein amount of the eluate fractions is quantitated and peak fractions are concentrated by ultrafiltration and further purified by size exclusion chromatography (SEC).

Employing the aforementioned methods, recombinant LIGHT receptor agonist fusion proteins (PROTEIN-A, SEQ ID NO: 15 and PROTEIN-B, SEQ ID NO: 31) were expressed in CHO-S cells and purified employing affinity chromatography.

Figure 6:
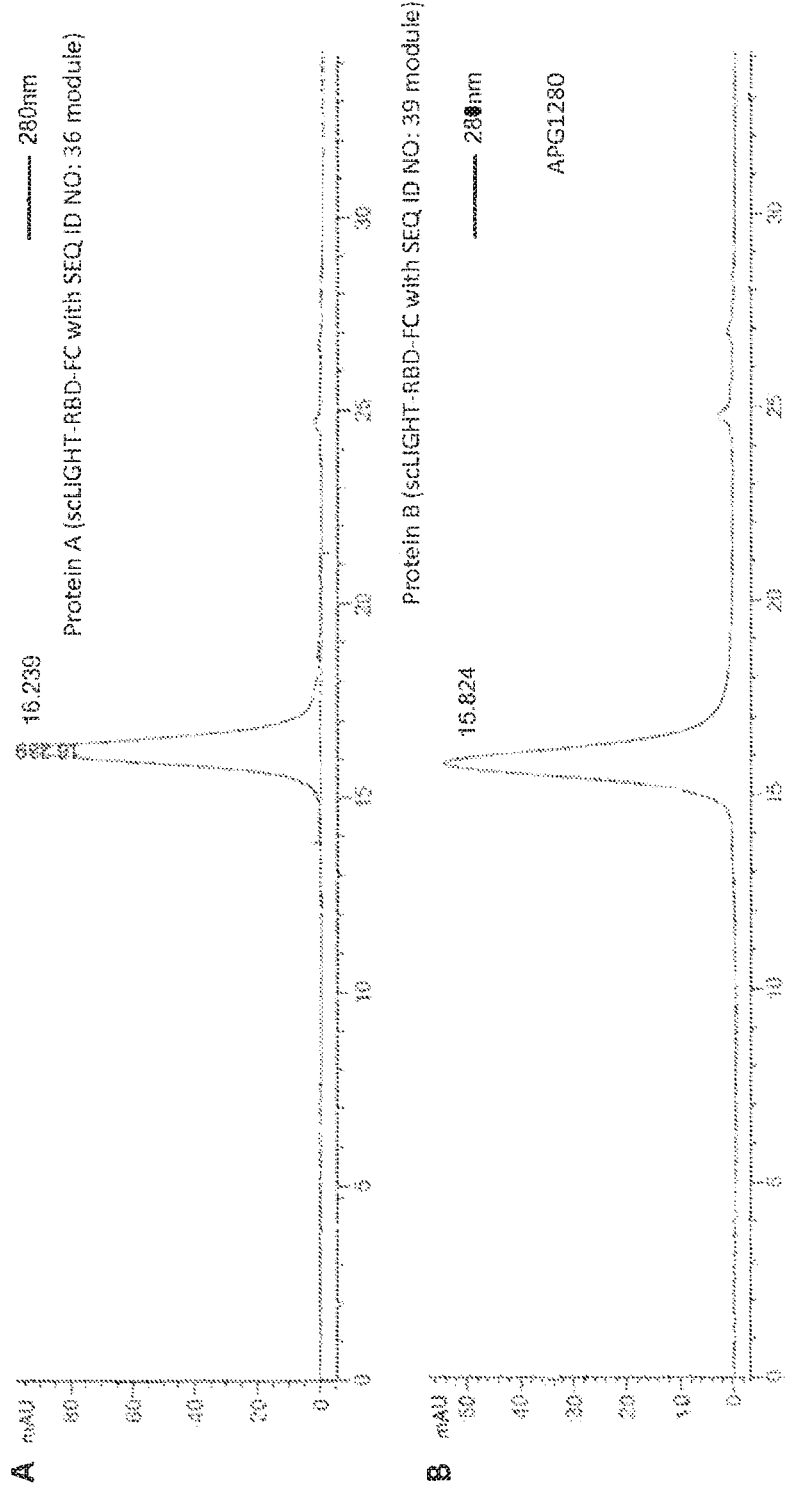
FIG. 6 Analytical size exclusion chromatography of PROTEIN A (A) and a PROTEIN B (B) performed on a 1260 Infinity HPLC system using a Tosoh TSKgelG3000SWxl column. The column was loaded with protein at a concentration of 0.94 mg/ml (A) or 0.77 mg/ml (B) in a total volume of 20 μl. The flow rate was set to 0.5 ml/min. One observes a single main peak at 16.239 (A) and 15.842 min (B).

Analytical size exclusion chromatography of PROTEIN A with asymmetric linker and shortened LIGHT domains (SEQ ID NO: 15) and PROTEIN B with symmetric linkers both glycosylated and (Refers to SEQ ID NO: 31) is shown in FIG. 6.

The SEC was performed on a 1260 Infinity HPLC system using a Tosoh TSKgelG3000SWxl column. The column was loaded with protein at a concentration of 0.94 mg/ml (A) or 0.77 mg/ml (B) in a total volume of 20 μl. The flow rate was set to 0.5 ml/min. One observes a single main peak at 16.24 min for PROTEIN A (FIG. 6, Part A) and 15.84 min for PROTEIN B (FIG. 6, Part B). Consequently, PROTEIN B has a higher apparent molecular weight due to the glycosylated linker (iv). Both proteins were prepared by AFC only, indicating due to the absence of aggregates high solubility. Protein A By using an internal molecular weight standard (BioRad SEC Standard) one can intrapolate the molecular weight of PROTEIN A and PROTEIN B from respective retention times.

For determination of the apparent molecular weight of purified fusion polypeptide under native conditions a Superdex 200 column was loaded with standard proteins of known molecular weight. Based on the elution volume of the standard proteins a calibration curve was plotted and the apparent molecular weight of purified fusion polypeptide was determined. The FC-domain comprising LIGHT receptor agonist fusion proteins typically eluted from the Superdex200 columns with an apparent molecular weight of approx. 160-180 kDa confirming the homodimerisation of the mature LIGHT receptor agonist fusion polypeptides by the Fc domain.

Example 3

Determination of Temperature Stability

The stability of PROTEIN A (scLIGHT-RBD-Fc) upon elevated temperatures was assessed. Therefore, this protein was exposed for 10 min in an incubator for the indicated temperatures and then cooled on ice. The binding activity towards its receptor HVEM was then assessed employing the following ELISA assay:

Plates were coated with HVEM-Fc. PROTEIN A (heat treated and non-treated control) was added to the plate and then detected via its Strep-Tag employing StrepTactin-HRP. Binding activity of the non-treated control was set as 100%. Values below 100% indicate a loss in binding activity towards the receptor.

The results from the temperature stability evaluation for PROTEIN A at concentration of 75 ng/ml are summarized in the following

|  | PROTEIN A (scLIGHT-RBD-Fc) Relative Binding to Receptor [%] |
| --- | --- |
| Control | 100 |
| 50° C. | 87 |
| 60° C. | 91 |
| 70° C. | 95 |
| 80° C. | 91 |

Surprisingly, PROTEIN A (scLIGHT-RBD-Fc) is very stable upon exposure to elevated temperatures. Even for an incubation at 80° C. for 10 minutes, no relevant decrease in binding to the receptor HVEM was observed.

Example 4

Trivalent Control Protein

To compare the relative binding between hexavalent LIGHT receptor agonist fusion proteins and the, trivalent LIGHT-RBD stabilized with bacteriophage RB69-FOLDON, PROTEIN X (SEQ ID NO: 38) was expressed in CHO-S cells and purified as described in the former section. The SEC-purified protein is served as control in the following Examples. The sequence of PROTEIN X (SEQ ID NO: 38) is shown in Table 7. Amino-acids 1-20 of PROTEIN X represent the signal peptide and the mature proteins starts with amino acid Glu51. This protein consists of three identical polypeptides each comprising one soluble LIGHT domain (E91-V240 of SEQ ID NO: 1); this assembly stabilized by the trimerization domain of bacteriophage RB69 fibritin fused with a flexible linker to the C-terminus of LIGHT.

TABLE 7

Trivalent control protein including a signal peptide

| SEQ ID NO | Sequence |
|---|---|
| 38 (Protein X) | METDTLLVFVLLVWVPAGNGEVNPAAHLTGANSSLTGSGGPLLW ETQLGLAFLRGLSYHDGALVVTKAGYYYIYSKVQLGGVGCPLGL ASTITHGLYKRTPRYPEELELLVSQQSPCGRATSSSRVWWDSSF LGGVVHLEAGEEVVVRVLDERLVRLRDGTRSYFGAFMVGSGSSG SSGSSGSGYIEDAPSDGKFYVRKDGAWVELPTASGPSSSSSSAW SHPQFEK. |

Example 5

Determination of the In Vitro Stability of LIGHT Receptor Agonist Proteins by Limited Protease Digestion All LIGHT receptor agonist proteins to be investigated will be expressed and purified as hexavalent Fc-Fusion protein as described in Example 1. The set will include LIGHT receptor agonist proteins comprising the N297S mutation [according to the EU numbering system] in the CH2-domain and a hinge region that enables the formation of three disulfide bridges and additionally lack the upper hinge lysine [K223, according to the EU numbering system] which is mutated to glycine [K223G]. In a limited protease digestion assay, the aforementioned LIGHT receptor agonist proteins comprising the N297S mutation and the K223G mutation simultaneously in context of a three disulfide enabling hinge will be compared to LIGHT receptor agonist proteins comprising the N297S mutation but have the K223 wildtype present either in the context of a two disulfide or three disulfide enabling hinge region.

In addition, LIGHT receptor agonist proteins with the second linker element (iv) reduced to 4 amino-acids and the shortened hinge element (vi) will be investigated. Both engineering strategies (N297S combined with K223G mutation in context of a three disulfide enabling hinge region) and shortage of linker elements (iv and vi) have a potential impact on the stability of the respective molecules.

The stability of different LIGHT receptor agonistic proteins of the present invention can be addressed by limited protease digestion in vitro. For this analysis, the aforementioned LIGHT receptor agonist proteins are incubated with low concentrations of proteases (e.g. Trypsin, V8 protease) at different temperatures (e.g. 4° C., 25° C., 37° C.) for different amounts of time. Quantification of specific proteolytic fragments and their appearance over time can be subsequently measured by different methods, like SDS-PAGE, analytical SEC or analytical Mass-Spectrometry methods known in the art (e.g Nano-RP-HPLC-ESI-MSMS). As the investigated proteins have most of their sequences in common, the faster appearance and enlarged quantities of specific proteolytic fragments from individual proteins over time can then be used to judge their relative stability and rank them to each other. With regard to protease based decoy kinetics of the aforementioned LIGHT receptor agonist proteins investigated, the following order regarding their proteolytic stability is to be expected:

The LIGHT receptor agonist proteins comprising the N297S and the K223G and the three disulfide enabling hinge region simultaneously have a prolonged stability as compared to the LIGHT receptor agonist proteins comprising the N297S and wildtype K223 in the hinge region. The LIGHT receptor agonist proteins comprising the SEQ ID NO: 21 as hinge linker have a prolonged stability as compared to LIGHT receptor agonist proteins comprising the SEQ ID NO: 16 as hinge linker element.

Example 6

Half-Life Determination

Molecule PROTEIN A is made up of two polypeptides covalently linked by three interchain disulfide bonds and comprises the K223G mutation in the hinge linker as well as the N297S mutation the Fc region (according to the EU numbering), resulting in aglycosylation of the CH2 domain. The purified PROTEIN-A was tested on the half-life in mice.

Female CD1 mice were administered with 1.0 mg/kg of PROTEIN A as a single intravenous bolus injection. Whole blood was collected before application (pre-dose), and up to 312 hours after test item administration. Serum was prepared and samples were stored at −80° C. until determination of serum concentrations.

Quantitation of the PROTEIN A concentrations in mouse serum was performed with an ELISA-assay detecting the HVEM agonist shown in Table 8. Plates were coated with HVEM-Fc. LIGHT constructs specifically binding to its receptor HVEM were then detected via their Strep-Tag employing StrepTactin-HRP. ELISA assays were carried out using reference PROTEIN A as calibration and control samples. The measured data of the standard concentrations were used to create calibration curves using a 5-parameter fit. This enabled the determination of the unknown PROTEIN A concentrations in the respective mouse serum samples.

Pharmacokinetic parameters were calculated using the mean serum concentrations and the pharmacokinetic evaluation program PK Solutions Version 2.0 for non-compartmental pharmacokinetic data analysis (Summit Research Services, Montrose, Colo.). PK Solutions is an automated, Excel-based application, which computes pharmacokinetic parameters from concentration-time data obtained from analysis of e.g. biological samples following intravenous or extra-vascular routes of administration. PK Solutions calculates results without presuming any specific compartmental model.

The results from the pharmacokinetics evaluation are summarized in Table 8.

TABLE 8

Results of the exploratory PK study in CD1-mice: single intravenous dose of 1 mg/kg of PROTEIN A.

|  | PROTEIN A |
|---|---|
| $t_{max}$ (h) | 0.083 |
| $C_{max}$ (µg/ml) | 12.8 |
| $t_{last}$ (h) | 192 |
| $C_{last}$ (µg/ml) | 0.141 |
| $t_{1/2}$ E (h) | 36.47 |
| $t_{1/2}$ E (d) | 1.52 |
| $AUC_{0-t}$ (µg*h/ml) | 346 |
| $AUC_{0-inf}$ (µg*h/ml) | 353 |

The results show that PROTEIN A has a surprisingly short terminal half-life of 36.47 hours in mice. This short half-life constitutes a favorable therapeutic option since a short co-stimulatory stimulus with LIGHT receptor agonist proteins is desirable.

Example 7

Stability/Aggregation Test

The contents of monomers and aggregates are determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a Superdex200 column (GE Healthcare). This column separates proteins in the range between 10 to 800 kDa.

For determination of the apparent molecular weight of purified fusion polypeptide under native conditions a Superdex 200 column is loaded with standard proteins of known molecular weight. Based on the elution volume of the standard proteins a calibration curve is plotted and the apparent molecular weight of purified fusion proteins of unknown molecular weight is calculated based on the elution volume.

SEC analysis of soluble, non-aggregated protein typically shows a distinct single protein peak at a defined elution volume (measured at OD at 280 nm or at OD 214 nm). This elution volume corresponds to the apparent native molecular weight of the particular protein. With regard to the definition of "monomer" in the case of FC-fusion proteins, the assembly of two polypeptide-chains is driven by the FC-part of the protein and the functional unit is a protein consisting of two chains. This unit that contains two FC-linked polypeptide chains is defined as "monomer" in the case of Fc-fusion proteins regardless of being a dimerized single-chain fusion polypeptide.

If protein aggregation occurs, the SEC analysis shows additional protein peaks with lower retention volumes. Protein oligomers potentially serve as aggregation seeds and a high content of oligomers potentially leads to aggregation of the protein. Oligomers of large molecular weight and aggregates elute in the void volume of the Superdex200 column and cannot be analyzed by SEC with respect to their native molecular weight.

Purified preparations of LIGHT receptor agonist fusion proteins should preferably contain only defined monomeric protein and only a very low amount of oligomeric protein. The degree of aggregation/oligomerization of a particular LIGHT receptor agonist fusion protein preparation is determined on basis of the SEC analysis by calculating the peak areas of the OD280 diagram for the defined monomer and the oligomer/aggregate fraction, respectively. Based on the total peak area the percentage of defined monomer protein is calculated as follows:

monomer content [%]=[Peak area monomer protein]/ [Total peak area]×100)

Example 8

Determination of the Equilibrium Binding Constants for Tri- and Hexavalent Light-receptor Ligand Constructs by QCM Analysis The equilibrium binding constants ($K_D$) of trivalent and hexavalent PROTEIN X and PROTEIN A are calculated based on kinetic binding data ($k_{on}$ and $k_{off}$) that are determined with an automated biosensor system (Attana A100). The A100 allows to investigate molecular interactions in real-time based on the Quartz Crystal Microbalance (QCM) technique.

For this purpose, the human LIGHT-receptor is immobilized to the surface of a carboxyl-activated QCM-chip. Subsequently the tri- or hexavalent PROTEIN X or PROTEIN A, respectively, is used as an analyte at different concentrations (e.g. 0.5, 1, 2, 5, and 10 µg/ml) for analyzing the kinetic binding data for ligand-receptor binding ($k_{on}$) and dissociation ($k_{off}$). The analysis is done in real time and the respective $K_D$ can be calculated: $K_D = k_{off}/k_{on}$.

The QCM analysis shows that the trivalent PROTEIN X binds to the respective immobilized LIGHT-receptor with a $K_D$ in the low nM-range with an expected $K_D$ of 1-100 nm. However, hexavalent constructs of PROTEIN A show a higher binding affinity in the pM-range towards the respective immobilized LIGHT-receptor with an expected $K_D$ of 1-1000 pM. A common characteristic of the kinetic binding data ($k_{on}$ and $k_{off}$) is that the hexavalent constructs show faster $k_{on}$ in comparison to the trivalent constructs. In addition, slower dissociation ($k_{off}$) is commonly observed for the hexavalent ligands if compared to the trivalent ligand.

Example 9

Apoptosis Induction by Tri- and Hexavalent Light-receptor Ligand Constructs in Human Breast and Colon Carcinoma Cells The human breast cancer cell line MDA-MB-231 and the human colon cancer cell line HT-29 are incubated with PROTEIN X and PROTEIN A at varying concentrations (between 0.1 ng/ml and 100 µg/ml) in combination with varying amounts of IFNγ (1-100 U/ml). Cells are incubated at 37° C. in the presence of IFNγ and PROTEIN X or PROTEIN A for 24 h, 48 h or 72 h. At each time point cells are harvested and processed for flow cytometric analysis assessing the binding of Propidium Iodide (PI) to double-stranded nucleic acids such as DNA and the upregulation of Annexin V. Both binding of PI and Annexin V upregulation are critical indicators for the induction of apoptotic cell death.

One expects to observe a supplementary effect exerted by PROTEIN A and PROTEIN X in a sense that both PROTEIN A and PROTEIN X will significantly increase the PI and Annexin V double-positive cell populations when compared to cells incubated with IFNγ or PROTEIN A or PROTEIN X alone. This supplementary effect is likely to hold true for both MDA-MB-231 and HT-29 cells, but can be more significant in the case of HT-29 cells. This implies that PROTEIN X and PROTEIN A can drive certain human cancer cell lines into apoptosis in the presence of IFNγ.

Example 10

Human In Vitro T Cell Proliferation Assay

Total T cells (human) purified by negative selection and magnetic beads (pan T cell isolation kit, Miltenyi Biotec) from the peripheral blood of healthy donors and stained with CFSE (CellTrace™ CFSE Cell Proliferation Kit, for flow cytometry, ThermoFisher) and seeded into 24-well plates at 2×10e6 cells per well. Cells were incubated at 37° C. for 5 days with media alone, soluble anti-CD3 antibody (clone OKT3 at 1 µg/ml) alone, anti-CD3 antibody plus anti-CD28 antibody (clone 28.2 at 1 µg/ml) or anti-CD3 antibody plus mature Protein A (SEQ ID NO:27) at 10, 100 or 1000 ng/ml, respectively.

On day 5, cells were washed and stained with DAPI (to exclude dead cells) and specific antibodies. Expression of Forward Scatter (FSC or size) and CFSE dilution (a measurement of proliferation) was measured by flow cytometry with a Guava EasyCyte 12 Flow Cytometer (EMD Millipore). Data analysis was performed on a minimum of ten thousand recorded events per sample with FlowJo 10.1 software (FlowJo, LLC). The percentage of responding cells was determined by gating on Forward Scatter and CFSE using the media control to determine proper gate location. Cells that had either increased cell size or decreased CFSE levels were labeled as responding cells. The individual data from two biological replicates from one donor is shown in table "Quantification of T cell activation" (below). These results are consistent with results from additional donors.

This data clearly shows that treatment of human T cells in vitro with Protein A enhances T cell activation and proliferation as compared to antibody stimulation alone.

Quantification of T Cell Activation:

| | Human T cell activation following treatment with Protein A in vitro | |
|---|---|---|
| | % of cells responding | |
| Stimulation | Sample 1 | Sample 2 |
| Media | 3 | 3 |
| anti-CD3 | 56 | 62 |
| anti-CD3/28 | 87 | 85 |
| anti-CD3 + Protein A 10 ng/ml | 69 | 58 |
| anti-CD3 + Protein A 100 ng/ml | 68 | 66 |
| anti-CD3 + Protein A 1000 ng/ml | 59 | 57 |

The invention claimed is:

1. A LIGHT receptor agonist protein comprising a single-chain fusion polypeptide comprising the amino acid sequence of any one of SEQ ID NOs: 15, 25, 27, 28, and 30-35.

2. The LIGHT receptor agonist protein of claim 1, which additionally comprises an N-terminal signal peptide domain, and/or which additionally comprises a C-terminal element comprising a recognition or a purification domain.

3. The LIGHT receptor agonist protein of claim 1, comprising two polypeptides each having the amino acid sequence as set forth in SEQ ID NO: 27, 30, 31, 32, 33, 34 or 35.

4. The LIGHT receptor agonist protein of claim 3, wherein the two polypeptides are covalently linked through three interchain disulfide bonds formed at:
   a) positions 468, 474 and 477 of SEQ ID NO: 27 or 30 or
   b) positions 474, 480 and 483 of SEQ ID NO: 31, or
   c) positions 465, 471 and 474 of SEQ ID NO: 32, or
   d) positions 472, 478 and 481 of SEQ ID NO: 33, 34, or
   e) positions 469, 475, 478 of SEQ ID NO: 35.

5. The LIGHT receptor agonist protein of claim 3, comprising one or more N-glycosylated asparagine residues selected from the group of N156 of SEQ ID NOs: 27, 30 and 32, N156 and N312 of SEQ ID NO: 31, and N156 and N311 of SEQ ID NO: 33, 34 and 35.

6. The LIGHT receptor agonist protein of claim 1, wherein the polypeptide is further post-translationally modified.

7. The LIGHT receptor agonist protein of claim 6, wherein the post-translational modification comprises modification of the N-terminal glutamine to pyroglutamate.

8. A pharmaceutical or diagnostic composition comprising as an active agent the LIGHT receptor agonist protein of claim 1, and one or more pharmaceutically acceptable carriers, diluents, excipients and/or adjuvants.

9. A nucleic acid molecule encoding the LIGHT receptor agonist protein of claim 1, in operative linkage with an expression control sequence.

10. An expression vector comprising the nucleic acid molecule of claim 9.

* * * * *

SEQUENCE LISTING

```
<160> NUMBER OF SEQ ID NOS: 40

<210> SEQ ID NO 1
<211> LENGTH: 240
<212> TYPE: PRT
<213> ORGANISM: Homo sapiens
<220> FEATURE:
<223> OTHER INFORMATION: LIGHT ligand (wt)

<400> SEQUENCE: 1

Met Glu Glu Ser Val Val Arg Pro Ser Val Phe Val Val Asp Gly Gln
 1               5                  10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Leu Met Gly
            35                  40                  45

Ala Gly Leu Ala Val Gln Gly Trp Phe Leu Leu Gln Leu His Trp Arg
        50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175
```

```
Leu Glu Leu Leu Val Ser Gln Gln Ser Pro Cys Gly Arg Ala Thr Ser
            180                 185                 190

Ser Ser Arg Val Trp Trp Asp Ser Phe Leu Gly Val Val His
        195                 200                 205

Leu Glu Ala Gly Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 2
<211> LENGTH: 8
<212> TYPE: PRT
<213> ORGANISM: Artificial Sequence
<220> FEATURE:
<223> OTHER INFORMATION: linker

<400> SEQUENCE: 2

Gly Ser Gly Ser Gly Asn Gly Ser
1               5

<210> SEQ ID NO 3
<211> LENGTH: 8
<212> TYPE: PRT
<213> ORGANISM: Artificial Sequence
<220> FEATURE:
<223> OTHER INFORMATION: linker

<400> SEQUENCE: 3

Gly Ser Gly Ser Gly Ser Gly Ser
1               5

<210> SEQ ID NO 4
<211> LENGTH: 8
<212> TYPE: PRT
<213> ORGANISM: Artificial Sequence
<220> FEATURE:
<223> OTHER INFORMATION: linker

<400> SEQUENCE: 4

Gly Gly Ser Gly Ser Gly Ser Gly
1               5

<210> SEQ ID NO 5
<211> LENGTH: 6
<212> TYPE: PRT
<213> ORGANISM: Artificial Sequence
<220> FEATURE:
<223> OTHER INFORMATION: linker

<400> SEQUENCE: 5

Gly Gly Ser Gly Ser Gly
1               5

<210> SEQ ID NO 6
<211> LENGTH: 4
<212> TYPE: PRT
<213> ORGANISM: Artificial Sequence
<220> FEATURE:
<223> OTHER INFORMATION: linker

<400> SEQUENCE: 6

Gly Gly Ser Gly
1

<210> SEQ ID NO 7
```

```
<211> LENGTH: 8
<212> TYPE: PRT
<213> ORGANISM: Artificial Sequence
<220> FEATURE:
<223> OTHER INFORMATION: linker

<400> SEQUENCE: 7

Gly Gly Ser Gly Asn Gly Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Gly Asn Gly Ser Gly Ser Gly
1               5

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Gly Gly Asn Gly Ser Gly
1               5

<210> SEQ ID NO 10
<211> LENGTH: 6
<212> TYPE: PRT
<213> ORGANISM: Artificial Sequence
<220> FEATURE:
<223> OTHER INFORMATION: linker

<400> SEQUENCE: 10

Gly Ser Gly Ser Gly Ser
1               5

<210> SEQ ID NO 11
<211> LENGTH: 4
<212> TYPE: PRT
<213> ORGANISM: Artificial Sequence
<220> FEATURE:
<223> OTHER INFORMATION: linker

<400> SEQUENCE: 11

Gly Ser Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: linker

<400> SEQUENCE: 12

Gly Ser Gly
1

<210> SEQ ID NO 13
<211> LENGTH: 218
```

```
<212> TYPE: PRT
<213> ORGANISM: Artificial Sequence
<220> FEATURE:
<223> OTHER INFORMATION: human IGG1 Fc N297S

<400> SEQUENCE: 13

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Ser Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 14
<211> LENGTH: 217
<212> TYPE: PRT
<213> ORGANISM: Artificial Sequence
<220> FEATURE:
<223> OTHER INFORMATION: human IGG1 Fc (wt)

<400> SEQUENCE: 14

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110
```

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 15
<211> LENGTH: 729
<212> TYPE: PRT
<213> ORGANISM: Artificial Sequence
<220> FEATURE:
<223> OTHER INFORMATION: PROTEIN A (LIGHT ligand fused to deglyco Fc)

<400> SEQUENCE: 15

Met Glu Thr Asp Thr Leu Leu Val Phe Val Leu Leu Val Trp Val Pro
1               5                   10                  15

Ala Gly Asn Gly Glu Val Asn Pro Ala Ala His Leu Thr Gly Ala Asn
            20                  25                  30

Ser Ser Leu Thr Gly Ser Gly Gly Pro Leu Leu Trp Glu Thr Gln Leu
        35                  40                  45

Gly Leu Ala Phe Leu Arg Gly Leu Ser Tyr His Asp Gly Ala Leu Val
    50                  55                  60

Val Thr Lys Ala Gly Tyr Tyr Tyr Ile Tyr Ser Lys Val Gln Leu Gly
65                  70                  75                  80

Gly Val Gly Cys Pro Leu Gly Leu Ala Ser Thr Ile Thr His Gly Leu
                85                  90                  95

Tyr Lys Arg Thr Pro Arg Tyr Pro Glu Glu Leu Glu Leu Leu Val Ser
            100                 105                 110

Gln Gln Ser Pro Cys Gly Arg Ala Thr Ser Ser Ser Arg Val Trp Trp
        115                 120                 125

Asp Ser Ser Phe Leu Gly Gly Val Val His Leu Glu Ala Gly Glu Glu
    130                 135                 140

Val Val Val Arg Val Leu Asp Glu Arg Leu Val Arg Leu Arg Asp Gly
145                 150                 155                 160

Thr Arg Ser Tyr Phe Gly Ala Phe Met Val Gly Ser Gly Ser Gly Asn
                165                 170                 175

Gly Ser Pro Ala Ala His Leu Thr Gly Ala Asn Ser Ser Leu Thr Gly
            180                 185                 190

Ser Gly Gly Pro Leu Leu Trp Glu Thr Gln Leu Gly Leu Ala Phe Leu
        195                 200                 205

Arg Gly Leu Ser Tyr His Asp Gly Ala Leu Val Val Thr Lys Ala Gly
    210                 215                 220

Tyr Tyr Tyr Ile Tyr Ser Lys Val Gln Leu Gly Gly Val Gly Cys Pro
225                 230                 235                 240

Leu Gly Leu Ala Ser Thr Ile Thr His Gly Leu Tyr Lys Arg Thr Pro
                245                 250                 255

-continued

Arg Tyr Pro Glu Glu Leu Glu Leu Leu Val Ser Gln Gln Ser Pro Cys
        260                 265                 270

Gly Arg Ala Thr Ser Ser Ser Arg Val Trp Trp Asp Ser Ser Phe Leu
        275                 280                 285

Gly Gly Val Val His Leu Glu Ala Gly Glu Val Val Val Arg Val
    290                 295                 300

Leu Asp Glu Arg Leu Val Arg Leu Arg Asp Gly Thr Arg Ser Tyr Phe
305                 310                 315                 320

Gly Ala Phe Met Val Gly Ser Gly Ser Pro Ala Ala His Leu Thr Gly
                325                 330                 335

Ala Asn Ser Ser Leu Thr Gly Ser Gly Gly Pro Leu Leu Trp Glu Thr
            340                 345                 350

Gln Leu Gly Leu Ala Phe Leu Arg Gly Leu Ser Tyr His Asp Gly Ala
        355                 360                 365

Leu Val Val Thr Lys Ala Gly Tyr Tyr Ile Tyr Ser Lys Val Gln
    370                 375                 380

Leu Gly Gly Val Gly Cys Pro Leu Gly Leu Ala Ser Thr Ile Thr His
385                 390                 395                 400

Gly Leu Tyr Lys Arg Thr Pro Arg Tyr Pro Glu Glu Leu Glu Leu Leu
                405                 410                 415

Val Ser Gln Gln Ser Pro Cys Gly Arg Ala Thr Ser Ser Ser Arg Val
            420                 425                 430

Trp Trp Asp Ser Ser Phe Leu Gly Gly Val Val His Leu Glu Ala Gly
        435                 440                 445

Glu Glu Val Val Val Arg Val Leu Asp Glu Arg Leu Val Arg Leu Arg
    450                 455                 460

Asp Gly Thr Arg Ser Tyr Phe Gly Ala Phe Met Val Gly Ser Ser Ser
465                 470                 475                 480

Ser Ser Ser Ser Ser Gly Ser Cys Asp Lys Thr His Thr Cys Pro Pro
                485                 490                 495

Cys Pro Ala Pro Glu Leu Leu Gly Gly Pro Ser Val Phe Leu Phe Pro
            500                 505                 510

Pro Lys Pro Lys Asp Thr Leu Met Ile Ser Arg Thr Pro Glu Val Thr
        515                 520                 525

Cys Val Val Val Asp Val Ser His Glu Asp Pro Glu Val Lys Phe Asn
    530                 535                 540

Trp Tyr Val Asp Gly Val Glu Val His Asn Ala Lys Thr Lys Pro Arg
545                 550                 555                 560

Glu Glu Gln Tyr Ser Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Tyr Thr Leu Pro Pro Ser Arg Glu
    610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

-continued

Phe Leu Tyr Ser Lys Leu Thr Val Asp Lys Ser Arg Trp Gln Gln Gly
            675                 680                 685

Asn Val Phe Ser Cys Ser Val Met His Glu Ala Leu His Asn His Tyr
        690                 695                 700

Thr Gln Lys Ser Leu Ser Leu Ser Pro Gly Ser Ser Ser Ser Ser Ser
705                 710                 715                 720

Ala Trp Ser His Pro Gln Phe Glu Lys
                725

<210> SEQ ID NO 16
<211> LENGTH: 21
<212> TYPE: PRT
<213> ORGANISM: Artificial Sequence
<220> FEATURE:
<223> OTHER INFORMATION: hinge linker

<400> SEQUENCE: 16

Gly Ser Ser Ser Ser Ser Ser Ser Gly Ser Cys Asp Lys Thr His
1               5                   10                  15

Thr Cys Pro Pro Cys
            20

<210> SEQ ID NO 17
<211> LENGTH: 20
<212> TYPE: PRT
<213> ORGANISM: Artificial Sequence
<220> FEATURE:
<223> OTHER INFORMATION: universal signal peptide

<400> SEQUENCE: 17

Met Glu Thr Asp Thr Leu Leu Val Phe Val Leu Leu Val Trp Val Pro
1               5                   10                  15

Ala Gly Asn Gly
            20

<210> SEQ ID NO 18
<211> LENGTH: 15
<212> TYPE: PRT
<213> ORGANISM: Artificial Sequence
<220> FEATURE:
<223> OTHER INFORMATION: serine linker with strep tag

<400> SEQUENCE: 18

Ser Ser Ser Ser Ser Ser Ala Trp Ser His Pro Gln Phe Glu Lys
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: hinge linker

<400> SEQUENCE: 19

Gly Ser Ser Ser Ser Ser Ser Ser Gly Ser Cys Asp Lys Thr His Thr
1               5                   10                  15

Cys Pro Pro Cys
            20

<210> SEQ ID NO 20
<211> LENGTH: 19
<212> TYPE: PRT
<213> ORGANISM: Artificial Sequence
<220> FEATURE:

<223> OTHER INFORMATION: hinge linker

<400> SEQUENCE: 20

Gly Ser Ser Ser Ser Ser Ser Gly Ser Cys Asp Lys Thr His Thr Cys
1               5                   10                  15

Pro Pro Cys

<210> SEQ ID NO 21
<211> LENGTH: 18
<212> TYPE: PRT
<213> ORGANISM: Artificial Sequence
<220> FEATURE:
<223> OTHER INFORMATION: hinge linker

<400> SEQUENCE: 21

Gly Ser Ser Ser Ser Ser Gly Ser Cys Asp Lys Thr His Thr Cys Pro
1               5                   10                  15

Pro Cys

<210> SEQ ID NO 22
<211> LENGTH: 16
<212> TYPE: PRT
<213> ORGANISM: Artificial Sequence
<220> FEATURE:
<223> OTHER INFORMATION: hinge linker

<400> SEQUENCE: 22

Gly Ser Ser Ser Gly Ser Cys Asp Lys Thr His Thr Cys Pro Pro Cys
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: hinge linker

<400> SEQUENCE: 23

Gly Ser Ser Ser Gly Ser Cys Asp Lys Thr His Thr Cys Pro Pro Cys
1               5                   10                  15

Gly Ser

<210> SEQ ID NO 24
<211> LENGTH: 20
<212> TYPE: PRT
<213> ORGANISM: Artificial Sequence
<220> FEATURE:
<223> OTHER INFORMATION: hinge linker

<400> SEQUENCE: 24

Gly Ser Ser Ser Gly Ser Cys Asp Lys Thr His Thr Cys Pro Pro Cys
1               5                   10                  15

Gly Ser Gly Ser
            20

<210> SEQ ID NO 25
<211> LENGTH: 715
<212> TYPE: PRT
<213> ORGANISM: Artificial Sequence
<220> FEATURE:
<223> OTHER INFORMATION: PROTEIN A - no strep tag

<400> SEQUENCE: 25

Met Glu Thr Asp Thr Leu Leu Val Phe Val Leu Leu Val Trp Val Pro

```
1               5                   10                  15
Ala Gly Asn Gly Glu Val Asn Pro Ala Ala His Leu Thr Gly Ala Asn
            20                  25                  30
Ser Ser Leu Thr Gly Ser Gly Pro Leu Leu Trp Glu Thr Gln Leu
            35                  40                  45
Gly Leu Ala Phe Leu Arg Gly Leu Ser Tyr His Asp Gly Ala Leu Val
    50                  55                  60
Val Thr Lys Ala Gly Tyr Tyr Tyr Ile Tyr Ser Lys Val Gln Leu Gly
65                  70                  75                  80
Gly Val Gly Cys Pro Leu Gly Leu Ala Ser Thr Ile Thr His Gly Leu
                85                  90                  95
Tyr Lys Arg Thr Pro Arg Tyr Pro Glu Glu Leu Glu Leu Leu Val Ser
            100                 105                 110
Gln Gln Ser Pro Cys Gly Arg Ala Thr Ser Ser Ser Arg Val Trp Trp
            115                 120                 125
Asp Ser Ser Phe Leu Gly Gly Val Val His Leu Glu Ala Gly Glu Glu
    130                 135                 140
Val Val Val Arg Val Leu Asp Glu Arg Leu Val Arg Leu Arg Asp Gly
145                 150                 155                 160
Thr Arg Ser Tyr Phe Gly Ala Phe Met Val Gly Ser Gly Ser Gly Asn
                165                 170                 175
Gly Ser Pro Ala Ala His Leu Thr Gly Ala Asn Ser Ser Leu Thr Gly
            180                 185                 190
Ser Gly Gly Pro Leu Leu Trp Glu Thr Gln Leu Gly Leu Ala Phe Leu
            195                 200                 205
Arg Gly Leu Ser Tyr His Asp Gly Ala Leu Val Val Thr Lys Ala Gly
    210                 215                 220
Tyr Tyr Tyr Ile Tyr Ser Lys Val Gln Leu Gly Gly Val Gly Cys Pro
225                 230                 235                 240
Leu Gly Leu Ala Ser Thr Ile Thr His Gly Leu Tyr Lys Arg Thr Pro
                245                 250                 255
Arg Tyr Pro Glu Glu Leu Glu Leu Leu Val Ser Gln Gln Ser Pro Cys
            260                 265                 270
Gly Arg Ala Thr Ser Ser Ser Arg Val Trp Trp Asp Ser Ser Phe Leu
            275                 280                 285
Gly Gly Val Val His Leu Glu Ala Gly Glu Glu Val Val Val Arg Val
    290                 295                 300
Leu Asp Glu Arg Leu Val Arg Leu Arg Asp Gly Thr Arg Ser Tyr Phe
305                 310                 315                 320
Gly Ala Phe Met Val Gly Ser Gly Ser Pro Ala Ala His Leu Thr Gly
                325                 330                 335
Ala Asn Ser Ser Leu Thr Gly Ser Gly Gly Pro Leu Leu Trp Glu Thr
            340                 345                 350
Gln Leu Gly Leu Ala Phe Leu Arg Gly Leu Ser Tyr His Asp Gly Ala
            355                 360                 365
Leu Val Val Thr Lys Ala Gly Tyr Tyr Tyr Ile Tyr Ser Lys Val Gln
    370                 375                 380
Leu Gly Gly Val Gly Cys Pro Leu Gly Leu Ala Ser Thr Ile Thr His
385                 390                 395                 400
Gly Leu Tyr Lys Arg Thr Pro Arg Tyr Pro Glu Glu Leu Glu Leu Leu
                405                 410                 415
Val Ser Gln Gln Ser Pro Cys Gly Arg Ala Thr Ser Ser Ser Arg Val
            420                 425                 430
```

Trp Trp Asp Ser Ser Phe Leu Gly Gly Val Val His Leu Glu Ala Gly
            435                 440                 445

Glu Glu Val Val Arg Val Leu Asp Glu Arg Leu Val Arg Leu Arg
    450                 455                 460

Asp Gly Thr Arg Ser Tyr Phe Gly Ala Phe Met Val Gly Ser Ser
465                 470                 475                 480

Ser Ser Ser Ser Gly Ser Cys Asp Lys Thr His Thr Cys Pro Pro
            485                 490                 495

Cys Pro Ala Pro Glu Leu Leu Gly Gly Pro Ser Val Phe Leu Phe Pro
                500                 505                 510

Pro Lys Pro Lys Asp Thr Leu Met Ile Ser Arg Thr Pro Glu Val Thr
            515                 520                 525

Cys Val Val Val Asp Val Ser His Glu Asp Pro Glu Val Lys Phe Asn
            530                 535                 540

Trp Tyr Val Asp Gly Val Glu Val His Asn Ala Lys Thr Lys Pro Arg
545                 550                 555                 560

Glu Glu Gln Tyr Ser Ser Thr Tyr Arg Val Val Ser Val Leu Thr Val
            565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
            595                 600                 605

Gly Gln Pro Arg Glu Pro Gln Val Tyr Thr Leu Pro Pro Ser Arg Glu
            610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
            645                 650                 655

Asn Asn Tyr Lys Thr Thr Pro Pro Val Leu Asp Ser Asp Gly Ser Phe
            660                 665                 670

Phe Leu Tyr Ser Lys Leu Thr Val Asp Lys Ser Arg Trp Gln Gln Gly
            675                 680                 685

Asn Val Phe Ser Cys Ser Val Met His Glu Ala Leu His Asn His Tyr
            690                 695                 700

Thr Gln Lys Ser Leu Ser Leu Ser Pro Gly Lys
705                 710                 715

<210> SEQ ID NO 26
<211> LENGTH: 714
<212> TYPE: PRT
<213> ORGANISM: Artificial Sequence
<220> FEATURE:
<223> OTHER INFORMATION: SEQ36 fused to wtFc (incl. signal peptide; no
      strep tag)

<400> SEQUENCE: 26

Met Glu Thr Asp Thr Leu Leu Val Phe Val Leu Leu Val Trp Val Pro
1               5                   10                  15

Ala Gly Asn Gly Glu Val Asn Pro Ala Ala His Leu Thr Gly Ala Asn
            20                  25                  30

Ser Ser Leu Thr Gly Ser Gly Gly Pro Leu Leu Trp Glu Thr Gln Leu
        35                  40                  45

Gly Leu Ala Phe Leu Arg Gly Leu Ser Tyr His Asp Gly Ala Leu Val
    50                  55                  60

Val Thr Lys Ala Gly Tyr Tyr Tyr Ile Tyr Ser Lys Val Gln Leu Gly

```
              65                  70                  75                  80
Gly Val Gly Cys Pro Leu Gly Leu Ala Ser Thr Ile Thr His Gly Leu
                    85                  90                  95
Tyr Lys Arg Thr Pro Arg Tyr Pro Glu Glu Leu Glu Leu Leu Val Ser
                100                 105                 110
Gln Gln Ser Pro Cys Gly Arg Ala Thr Ser Ser Ser Arg Val Trp Trp
                115                 120                 125
Asp Ser Ser Phe Leu Gly Gly Val Val His Leu Glu Ala Gly Glu Glu
                130                 135                 140
Val Val Val Arg Val Leu Asp Glu Arg Leu Val Arg Leu Arg Asp Gly
145                 150                 155                 160
Thr Arg Ser Tyr Phe Gly Ala Phe Met Val Gly Ser Gly Ser Gly Asn
                165                 170                 175
Gly Ser Pro Ala Ala His Leu Thr Gly Ala Asn Ser Ser Leu Thr Gly
                180                 185                 190
Ser Gly Gly Pro Leu Leu Trp Glu Thr Gln Leu Gly Leu Ala Phe Leu
                195                 200                 205
Arg Gly Leu Ser Tyr His Asp Gly Ala Leu Val Val Thr Lys Ala Gly
                210                 215                 220
Tyr Tyr Tyr Ile Tyr Ser Lys Val Gln Leu Gly Gly Val Gly Cys Pro
225                 230                 235                 240
Leu Gly Leu Ala Ser Thr Ile Thr His Gly Leu Tyr Lys Arg Thr Pro
                245                 250                 255
Arg Tyr Pro Glu Glu Leu Glu Leu Leu Val Ser Gln Gln Ser Pro Cys
                260                 265                 270
Gly Arg Ala Thr Ser Ser Ser Arg Val Trp Trp Asp Ser Ser Phe Leu
                275                 280                 285
Gly Gly Val Val His Leu Glu Ala Gly Glu Glu Val Val Val Arg Val
                290                 295                 300
Leu Asp Glu Arg Leu Val Arg Leu Arg Asp Gly Thr Arg Ser Tyr Phe
305                 310                 315                 320
Gly Ala Phe Met Val Gly Ser Gly Ser Pro Ala Ala His Leu Thr Gly
                325                 330                 335
Ala Asn Ser Ser Leu Thr Gly Ser Gly Gly Pro Leu Leu Trp Glu Thr
                340                 345                 350
Gln Leu Gly Leu Ala Phe Leu Arg Gly Leu Ser Tyr His Asp Gly Ala
                355                 360                 365
Leu Val Val Thr Lys Ala Gly Tyr Tyr Tyr Ile Tyr Ser Lys Val Gln
                370                 375                 380
Leu Gly Gly Val Gly Cys Pro Leu Gly Leu Ala Ser Thr Ile Thr His
385                 390                 395                 400
Gly Leu Tyr Lys Arg Thr Pro Arg Tyr Pro Glu Glu Leu Glu Leu Leu
                405                 410                 415
Val Ser Gln Gln Ser Pro Cys Gly Arg Ala Thr Ser Ser Ser Arg Val
                420                 425                 430
Trp Trp Asp Ser Ser Phe Leu Gly Gly Val Val His Leu Glu Ala Gly
                435                 440                 445
Glu Glu Val Val Val Arg Val Leu Asp Glu Arg Leu Val Arg Leu Arg
                450                 455                 460
Asp Gly Thr Arg Ser Tyr Phe Gly Ala Phe Met Val Gly Ser Ser Ser
465                 470                 475                 480
Ser Ser Ser Ser Ser Gly Ser Cys Asp Lys Thr His Thr Cys Pro Pro
                485                 490                 495
```

```
Cys Pro Ala Pro Pro Val Ala Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Gly Leu Pro Ser Ser Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys
705                 710

<210> SEQ ID NO 27
<211> LENGTH: 695
<212> TYPE: PRT
<213> ORGANISM: Artificial Sequence
<220> FEATURE:
<223> OTHER INFORMATION: SEQ36 fused to deglyco-Fc (no strep tag)

<400> SEQUENCE: 27

Glu Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30

Leu Arg Gly Leu Ser Tyr His Asp Gly Ala Leu Val Val Thr Lys Ala
        35                  40                  45

Gly Tyr Tyr Tyr Ile Tyr Ser Lys Val Gln Leu Gly Val Gly Cys
    50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Ser Arg Val Trp Trp Asp Ser Ser Phe
            100                 105                 110

Leu Gly Gly Val Val His Leu Glu Ala Gly Glu Glu Val Val Val Arg
        115                 120                 125

Val Leu Asp Glu Arg Leu Val Arg Leu Arg Asp Gly Thr Arg Ser Tyr
    130                 135                 140
```

```
Phe Gly Ala Phe Met Val Gly Ser Gly Ser Gly Asn Gly Ser Pro Ala
145                 150                 155                 160

Ala His Leu Thr Gly Ala Asn Ser Ser Leu Thr Gly Ser Gly Gly Pro
            165                 170                 175

Leu Leu Trp Glu Thr Gln Leu Gly Leu Ala Phe Leu Arg Gly Leu Ser
        180                 185                 190

Tyr His Asp Gly Ala Leu Val Val Thr Lys Ala Gly Tyr Tyr Tyr Ile
        195                 200                 205

Tyr Ser Lys Val Gln Leu Gly Gly Val Gly Cys Pro Leu Gly Leu Ala
210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
            260                 265                 270

His Leu Glu Ala Gly Glu Val Val Arg Val Leu Asp Glu Arg
        275                 280                 285

Leu Val Arg Leu Arg Asp Gly Thr Arg Ser Tyr Phe Gly Ala Phe Met
        290                 295                 300

Val Gly Ser Gly Ser Pro Ala Ala His Leu Thr Gly Ala Asn Ser Ser
305                 310                 315                 320

Leu Thr Gly Ser Gly Gly Pro Leu Leu Trp Glu Thr Gln Leu Gly Leu
            325                 330                 335

Ala Phe Leu Arg Gly Leu Ser Tyr His Asp Gly Ala Leu Val Val Thr
            340                 345                 350

Lys Ala Gly Tyr Tyr Tyr Ile Tyr Ser Lys Val Gln Leu Gly Gly Val
            355                 360                 365

Gly Cys Pro Leu Gly Leu Ala Ser Thr Ile Thr His Gly Leu Tyr Lys
        370                 375                 380

Arg Thr Pro Arg Tyr Pro Glu Glu Leu Glu Leu Leu Val Ser Gln Gln
385                 390                 395                 400

Ser Pro Cys Gly Arg Ala Thr Ser Ser Ser Arg Val Trp Trp Asp Ser
            405                 410                 415

Ser Phe Leu Gly Gly Val Val His Leu Glu Ala Gly Glu Glu Val Val
            420                 425                 430

Val Arg Val Leu Asp Glu Arg Leu Val Arg Leu Arg Asp Gly Thr Arg
            435                 440                 445

Ser Tyr Phe Gly Ala Phe Met Val Gly Ser Ser Ser Ser Ser Ser Ser
        450                 455                 460

Ser Gly Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
            515                 520                 525

Gly Val Glu Val His Asn Ala Lys Thr Lys Pro Arg Glu Glu Gln Tyr
        530                 535                 540

Ser Ser Thr Tyr Arg Val Val Ser Val Leu Thr Val Leu His Gln Asp
545                 550                 555                 560
```

Trp Leu Asn Gly Lys Glu Tyr Lys Cys Lys Val Ser Asn Lys Ala Leu
                565                 570                 575
Pro Ala Pro Ile Glu Lys Thr Ile Ser Lys Ala Lys Gly Gln Pro Arg
            580                 585                 590
Glu Pro Gln Val Tyr Thr Leu Pro Pro Ser Arg Glu Glu Met Thr Lys
        595                 600                 605
Asn Gln Val Ser Leu Thr Cys Leu Val Lys Gly Phe Tyr Pro Ser Asp
    610                 615                 620
Ile Ala Val Glu Trp Glu Ser Asn Gly Gln Pro Glu Asn Asn Tyr Lys
625                 630                 635                 640
Thr Thr Pro Pro Val Leu Asp Ser Asp Gly Ser Phe Phe Leu Tyr Ser
                645                 650                 655
Lys Leu Thr Val Asp Lys Ser Arg Trp Gln Gln Gly Asn Val Phe Ser
            660                 665                 670
Cys Ser Val Met His Glu Ala Leu His Asn His Tyr Thr Gln Lys Ser
        675                 680                 685
Leu Ser Leu Ser Pro Gly Lys
    690                 695

<210> SEQ ID NO 28
<211> LENGTH: 709
<212> TYPE: PRT
<213> ORGANISM: Artificial Sequence
<220> FEATURE:
<223> OTHER INFORMATION: SEQ36 fused to deglyco-Fc (incl. strep tag)

<400> SEQUENCE: 28

Glu Val Asn Pro Ala Ala His Leu Thr Gly Ala Asn Ser Ser Leu Thr
1               5                   10                  15
Gly Ser Gly Gly Pro Leu Leu Trp Glu Thr Gln Leu Gly Leu Ala Phe
            20                  25                  30
Leu Arg Gly Leu Ser Tyr His Asp Gly Ala Leu Val Val Thr Lys Ala
        35                  40                  45
Gly Tyr Tyr Tyr Ile Tyr Ser Lys Val Gln Leu Gly Gly Val Gly Cys
    50                  55                  60
Pro Leu Gly Leu Ala Ser Thr Ile Thr His Gly Leu Tyr Lys Arg Thr
65                  70                  75                  80
Pro Arg Tyr Pro Glu Glu Leu Glu Leu Leu Val Ser Gln Gln Ser Pro
                85                  90                  95
Cys Gly Arg Ala Thr Ser Ser Ser Arg Val Trp Trp Asp Ser Ser Phe
            100                 105                 110
Leu Gly Gly Val Val His Leu Glu Ala Gly Glu Glu Val Val Val Arg
        115                 120                 125
Val Leu Asp Glu Arg Leu Val Arg Leu Arg Asp Gly Thr Arg Ser Tyr
    130                 135                 140
Phe Gly Ala Phe Met Val Gly Ser Gly Ser Asn Gly Ser Pro Ala
145                 150                 155                 160
Ala His Leu Thr Gly Ala Asn Ser Ser Leu Thr Gly Ser Gly Gly Pro
                165                 170                 175
Leu Leu Trp Glu Thr Gln Leu Gly Leu Ala Phe Leu Arg Gly Leu Ser
            180                 185                 190
Tyr His Asp Gly Ala Leu Val Val Thr Lys Ala Gly Tyr Tyr Tyr Ile
        195                 200                 205
Tyr Ser Lys Val Gln Leu Gly Gly Val Gly Cys Pro Leu Gly Leu Ala
    210                 215                 220

-continued

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
            245                 250                 255

Ser Ser Ser Arg Val Trp Trp Asp Ser Ser Phe Leu Gly Gly Val Val
        260                 265                 270

His Leu Glu Ala Gly Glu Val Val Arg Val Leu Asp Glu Arg
    275                 280                 285

Leu Val Arg Leu Arg Asp Gly Thr Arg Ser Tyr Phe Gly Ala Phe Met
    290                 295                 300

Val Gly Ser Gly Ser Pro Ala Ala His Leu Thr Gly Ala Asn Ser Ser
305                 310                 315                 320

Leu Thr Gly Ser Gly Gly Pro Leu Leu Trp Glu Thr Gln Leu Gly Leu
            325                 330                 335

Ala Phe Leu Arg Gly Leu Ser Tyr His Asp Gly Ala Leu Val Val Thr
            340                 345                 350

Lys Ala Gly Tyr Tyr Ile Tyr Ser Lys Val Gln Leu Gly Gly Val
        355                 360                 365

Gly Cys Pro Leu Gly Leu Ala Ser Thr Ile Thr His Gly Leu Tyr Lys
370                 375                 380

Arg Thr Pro Arg Tyr Pro Glu Glu Leu Glu Leu Leu Val Ser Gln Gln
385                 390                 395                 400

Ser Pro Cys Gly Arg Ala Thr Ser Ser Ser Arg Val Trp Trp Asp Ser
            405                 410                 415

Ser Phe Leu Gly Gly Val Val His Leu Glu Ala Gly Glu Val Val
        420                 425                 430

Val Arg Val Leu Asp Glu Arg Leu Val Arg Leu Arg Asp Gly Thr Arg
        435                 440                 445

Ser Tyr Phe Gly Ala Phe Met Val Gly Ser Ser Ser Ser Ser Ser Ser
        450                 455                 460

Ser Gly Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
            485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
        515                 520                 525

Gly Val Glu Val His Asn Ala Lys Thr Lys Pro Arg Glu Glu Gln Tyr
        530                 535                 540

Ser Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
            565                 570                 575

Pro Ala Pro Ile Glu Lys Thr Ile Ser Lys Ala Lys Gly Gln Pro Arg
        580                 585                 590

Glu Pro Gln Val Tyr Thr Leu Pro Pro Ser Arg Glu Glu Met Thr Lys
        595                 600                 605

Asn Gln Val Ser Leu Thr Cys Leu Val Lys Gly Phe Tyr Pro Ser Asp
        610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser

```
                    645                 650                 655
Lys Leu Thr Val Asp Lys Ser Arg Trp Gln Gln Gly Asn Val Phe Ser
                660                 665                 670

Cys Ser Val Met His Glu Ala Leu His Asn His Tyr Thr Gln Lys Ser
            675                 680                 685

Leu Ser Leu Ser Pro Gly Ser Ser Ser Ser Ser Ala Trp Ser His
        690                 695                 700

Pro Gln Phe Glu Lys
705

<210> SEQ ID NO 29
<211> LENGTH: 694
<212> TYPE: PRT
<213> ORGANISM: Artificial Sequence
<220> FEATURE:
<223> OTHER INFORMATION: SEQ36 fused to wt-Fc (no signal peptide, no
      strep tag)

<400> SEQUENCE: 29

Glu Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30

Leu Arg Gly Leu Ser Tyr His Asp Gly Ala Leu Val Val Thr Lys Ala
        35                  40                  45

Gly Tyr Tyr Tyr Ile Tyr Ser Lys Val Gln Leu Gly Gly Val Gly Cys
    50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Arg Val Trp Trp Asp Ser Ser Phe
            100                 105                 110

Leu Gly Gly Val Val His Leu Glu Ala Gly Glu Val Val Val Arg
        115                 120                 125

Val Leu Asp Glu Arg Leu Val Arg Leu Arg Asp Gly Thr Arg Ser Tyr
    130                 135                 140

Phe Gly Ala Phe Met Val Gly Ser Gly Ser Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
            180                 185                 190

Tyr His Asp Gly Ala Leu Val Val Thr Lys Ala Gly Tyr Tyr Tyr Ile
        195                 200                 205

Tyr Ser Lys Val Gln Leu Gly Gly Val Gly Cys Pro Leu Gly Leu Ala
    210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
            260                 265                 270

His Leu Glu Ala Gly Glu Val Val Val Arg Val Leu Asp Glu Arg
        275                 280                 285
```

Leu Val Arg Leu Arg Asp Gly Thr Arg Ser Tyr Phe Gly Ala Phe Met
290                 295                 300

Val Gly Ser Gly Ser Pro Ala His Leu Thr Gly Ala Asn Ser Ser
305                 310                 315                 320

Leu Thr Gly Ser Gly Gly Pro Leu Leu Trp Glu Thr Gln Leu Gly Leu
            325                 330                 335

Ala Phe Leu Arg Gly Leu Ser Tyr His Asp Gly Ala Leu Val Val Thr
            340                 345                 350

Lys Ala Gly Tyr Tyr Ile Tyr Ser Lys Val Gln Leu Gly Gly Val
            355                 360                 365

Gly Cys Pro Leu Gly Leu Ala Ser Thr Ile Thr His Gly Leu Tyr Lys
370                 375                 380

Arg Thr Pro Arg Tyr Pro Glu Glu Leu Glu Leu Leu Val Ser Gln Gln
385                 390                 395                 400

Ser Pro Cys Gly Arg Ala Thr Ser Ser Arg Val Trp Trp Asp Ser
            405                 410                 415

Ser Phe Leu Gly Gly Val Val His Leu Glu Ala Gly Glu Glu Val Val
            420                 425                 430

Val Arg Val Leu Asp Glu Arg Leu Val Arg Leu Arg Asp Gly Thr Arg
            435                 440                 445

Ser Tyr Phe Gly Ala Phe Met Val Gly Ser Ser Ser Ser Ser Ser
450                 455                 460

Ser Gly Ser Cys Asp Lys Thr His Thr Cys Pro Pro Cys Pro Ala Pro
465                 470                 475                 480

Pro Val Ala Gly Pro Ser Val Phe Leu Phe Pro Pro Lys Pro Lys Asp
            485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
            515                 520                 525

Val Glu Val His Asn Ala Lys Thr Lys Pro Arg Glu Glu Gln Tyr Asn
            530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Gly Leu Pro
            565                 570                 575

Ser Ser Ile Glu Lys Thr Ile Ser Lys Ala Lys Gly Gln Pro Arg Glu
            580                 585                 590

Pro Gln Val Tyr Thr Leu Pro Pro Ser Arg Glu Glu Met Thr Lys Asn
            595                 600                 605

Gln Val Ser Leu Thr Cys Leu Val Lys Gly Phe Tyr Pro Ser Asp Ile
610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
            645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
            675                 680                 685

Ser Leu Ser Pro Gly Lys
690

<210> SEQ ID NO 30
<211> LENGTH: 695
<212> TYPE: PRT
<213> ORGANISM: Artificial Sequence
<220> FEATURE:
<223> OTHER INFORMATION: Seq27 with altered first RBD module E1Q (equals E91Q in Seq1)

<400> SEQUENCE: 30

```
Gln Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30

Leu Arg Gly Leu Ser Tyr His Asp Gly Ala Leu Val Val Thr Lys Ala
        35                  40                  45

Gly Tyr Tyr Tyr Ile Tyr Ser Lys Val Gln Leu Gly Gly Val Gly Cys
    50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Ser Arg Val Trp Trp Asp Ser Ser Phe
            100                 105                 110

Leu Gly Gly Val Val His Leu Glu Ala Gly Glu Glu Val Val Val Arg
        115                 120                 125

Val Leu Asp Glu Arg Leu Val Arg Leu Arg Asp Gly Thr Arg Ser Tyr
    130                 135                 140

Phe Gly Ala Phe Met Val Gly Ser Gly Ser Gly Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
            180                 185                 190

Tyr His Asp Gly Ala Leu Val Val Thr Lys Ala Gly Tyr Tyr Tyr Ile
        195                 200                 205

Tyr Ser Lys Val Gln Leu Gly Gly Val Gly Cys Pro Leu Gly Leu Ala
    210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
            260                 265                 270

His Leu Glu Ala Gly Glu Glu Val Val Val Arg Val Leu Asp Glu Arg
        275                 280                 285

Leu Val Arg Leu Arg Asp Gly Thr Arg Ser Tyr Phe Gly Ala Phe Met
    290                 295                 300

Val Gly Ser Gly Ser Pro Ala Ala His Leu Thr Gly Ala Asn Ser Ser
305                 310                 315                 320

Leu Thr Gly Ser Gly Gly Pro Leu Leu Trp Glu Thr Gln Leu Gly Leu
                325                 330                 335

Ala Phe Leu Arg Gly Leu Ser Tyr His Asp Gly Ala Leu Val Val Thr
            340                 345                 350

Lys Ala Gly Tyr Tyr Tyr Ile Tyr Ser Lys Val Gln Leu Gly Gly Val
        355                 360                 365
```

```
Gly Cys Pro Leu Gly Leu Ala Ser Thr Ile Thr His Gly Leu Tyr Lys
    370                 375                 380

Arg Thr Pro Arg Tyr Pro Glu Glu Leu Glu Leu Leu Val Ser Gln Gln
385                 390                 395                 400

Ser Pro Cys Gly Arg Ala Thr Ser Ser Ser Arg Val Trp Trp Asp Ser
                405                 410                 415

Ser Phe Leu Gly Gly Val Val His Leu Glu Ala Gly Glu Val Val
                420                 425                 430

Val Arg Val Leu Asp Glu Arg Leu Val Arg Leu Arg Asp Gly Thr Arg
                435                 440                 445

Ser Tyr Phe Gly Ala Phe Met Val Gly Ser Ser Ser Ser Ser Ser
    450                 455                 460

Ser Gly Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
                500                 505                 510

Asp Val Ser His Glu Asp Pro Glu Val Lys Phe Asn Trp Tyr Val Asp
                515                 520                 525

Gly Val Glu Val His Asn Ala Lys Thr Lys Pro Arg Glu Glu Gln Tyr
    530                 535                 540

Ser Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
                565                 570                 575

Pro Ala Pro Ile Glu Lys Thr Ile Ser Lys Ala Lys Gly Gln Pro Arg
                580                 585                 590

Glu Pro Gln Val Tyr Thr Leu Pro Pro Ser Arg Glu Glu Met Thr Lys
    595                 600                 605

Asn Gln Val Ser Leu Thr Cys Leu Val Lys Gly Phe Tyr Pro Ser Asp
610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser
                645                 650                 655

Lys Leu Thr Val Asp Lys Ser Arg Trp Gln Gln Gly Asn Val Phe Ser
                660                 665                 670

Cys Ser Val Met His Glu Ala Leu His Asn His Tyr Thr Gln Lys Ser
                675                 680                 685

Leu Ser Leu Ser Pro Gly Lys
    690                 695

<210> SEQ ID NO 31
<211> LENGTH: 701
<212> TYPE: PRT
<213> ORGANISM: Artificial Sequence
<220> FEATURE:
<223> OTHER INFORMATION: Seq39 fused to human IGG1 Fc of Seq13

<400> SEQUENCE: 31

Gln Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30
```

-continued

```
Leu Arg Gly Leu Ser Tyr His Asp Gly Ala Leu Val Thr Lys Ala
             35                  40                  45
Gly Tyr Tyr Tyr Ile Tyr Ser Lys Val Gln Leu Gly Gly Val Gly Cys
 50                      55                  60
Pro Leu Gly Leu Ala Ser Thr Ile Thr His Gly Leu Tyr Lys Arg Thr
 65                  70                  75                  80
Pro Arg Tyr Pro Glu Glu Leu Glu Leu Leu Val Ser Gln Gln Ser Pro
                 85                  90                  95
Cys Gly Arg Ala Thr Ser Ser Arg Val Trp Trp Asp Ser Ser Phe
                100                 105                 110
Leu Gly Gly Val Val His Leu Glu Ala Gly Glu Glu Val Val Arg
            115                 120                 125
Val Leu Asp Glu Arg Leu Val Arg Leu Arg Asp Gly Thr Arg Ser Tyr
130                 135                 140
Phe Gly Ala Phe Met Val Gly Ser Gly Ser Gly Asn Gly Ser Asn Pro
145                 150                 155                 160
Ala Ala His Leu Thr Gly Ala Asn Ser Ser Leu Thr Gly Ser Gly Gly
                165                 170                 175
Pro Leu Leu Trp Glu Thr Gln Leu Gly Leu Ala Phe Leu Arg Gly Leu
            180                 185                 190
Ser Tyr His Asp Gly Ala Leu Val Val Thr Lys Ala Gly Tyr Tyr Tyr
        195                 200                 205
Ile Tyr Ser Lys Val Gln Leu Gly Gly Val Gly Cys Pro Leu Gly Leu
    210                 215                 220
Ala Ser Thr Ile Thr His Gly Leu Tyr Lys Arg Thr Pro Arg Tyr Pro
225                 230                 235                 240
Glu Glu Leu Glu Leu Leu Val Ser Gln Gln Ser Pro Cys Gly Arg Ala
                245                 250                 255
Thr Ser Ser Arg Val Trp Trp Asp Ser Ser Phe Leu Gly Gly Val
            260                 265                 270
Val His Leu Glu Ala Gly Glu Glu Val Val Arg Val Leu Asp Glu
        275                 280                 285
Arg Leu Val Arg Leu Arg Asp Gly Thr Arg Ser Tyr Phe Gly Ala Phe
    290                 295                 300
Met Val Gly Ser Gly Ser Gly Asn Gly Ser Asn Pro Ala Ala His Leu
305                 310                 315                 320
Thr Gly Ala Asn Ser Ser Leu Thr Gly Ser Gly Gly Pro Leu Leu Trp
                325                 330                 335
Glu Thr Gln Leu Gly Leu Ala Phe Leu Arg Gly Leu Ser Tyr His Asp
            340                 345                 350
Gly Ala Leu Val Val Thr Lys Ala Gly Tyr Tyr Tyr Ile Tyr Ser Lys
        355                 360                 365
Val Gln Leu Gly Gly Val Gly Cys Pro Leu Gly Leu Ala Ser Thr Ile
    370                 375                 380
Thr His Gly Leu Tyr Lys Arg Thr Pro Arg Tyr Pro Glu Glu Leu Glu
385                 390                 395                 400
Leu Leu Val Ser Gln Gln Ser Pro Cys Gly Arg Ala Thr Ser Ser Ser
                405                 410                 415
Arg Val Trp Trp Asp Ser Ser Phe Leu Gly Gly Val Val His Leu Glu
            420                 425                 430
Ala Gly Glu Glu Val Val Arg Val Leu Asp Glu Arg Leu Val Arg
        435                 440                 445
Leu Arg Asp Gly Thr Arg Ser Tyr Phe Gly Ala Phe Met Val Gly Ser
```

```
                    450                 455                 460
Ser Ser Ser Ser Ser Ser Gly Ser Cys Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
                500                 505                 510

Val Thr Cys Val Val Val Asp Val Ser His Glu Asp Pro Glu Val Lys
            515                 520                 525

Phe Asn Trp Tyr Val Asp Gly Val Glu Val His Asn Ala Lys Thr Lys
            530                 535                 540

Pro Arg Glu Glu Gln Tyr Ser Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
            595                 600                 605

Arg Glu Glu Met Thr Lys Asn Gln Val Ser Leu Thr Cys Leu Val Lys
            610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
                660                 665                 670

Gln Gly Asn Val Phe Ser Cys Ser Val Met His Glu Ala Leu His Asn
            675                 680                 685

His Tyr Thr Gln Lys Ser Leu Ser Leu Ser Pro Gly Lys
            690                 695                 700

<210> SEQ ID NO 32
<211> LENGTH: 692
<212> TYPE: PRT
<213> ORGANISM: Artificial Sequence
<220> FEATURE:
<223> OTHER INFORMATION: Seq30 with shorter hinge linker

<400> SEQUENCE: 32

Gln Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
                20                  25                  30

Leu Arg Gly Leu Ser Tyr His Asp Gly Ala Leu Val Val Thr Lys Ala
            35                  40                  45

Gly Tyr Tyr Tyr Ile Tyr Ser Lys Val Gln Leu Gly Gly Val Gly Cys
        50                  55                  60

Pro Leu Gly Leu Ala Ser Thr Ile Thr His Gly Leu Tyr Lys Arg Thr
65              70                  75                  80

Pro Arg Tyr Pro Glu Glu Leu Glu Leu Leu Val Ser Gln Gln Ser Pro
                85                  90                  95

Cys Gly Arg Ala Thr Ser Ser Ser Arg Val Trp Trp Asp Ser Ser Phe
            100                 105                 110

Leu Gly Gly Val Val His Leu Glu Ala Gly Glu Glu Val Val Val Arg
```

```
              115                 120                 125
Val Leu Asp Glu Arg Leu Val Arg Leu Arg Asp Gly Thr Arg Ser Tyr
            130                 135                 140

Phe Gly Ala Phe Met Val Gly Ser Gly Ser Gly Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
                180                 185                 190

Tyr His Asp Gly Ala Leu Val Val Thr Lys Ala Gly Tyr Tyr Tyr Ile
                195                 200                 205

Tyr Ser Lys Val Gln Leu Gly Gly Val Gly Cys Pro Leu Gly Leu Ala
            210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
                260                 265                 270

His Leu Glu Ala Gly Glu Val Val Arg Val Leu Asp Glu Arg
                275                 280                 285

Leu Val Arg Leu Arg Asp Gly Thr Arg Ser Tyr Phe Gly Ala Phe Met
            290                 295                 300

Val Gly Ser Gly Ser Pro Ala Ala His Leu Thr Gly Ala Asn Ser Ser
305                 310                 315                 320

Leu Thr Gly Ser Gly Gly Pro Leu Leu Trp Glu Thr Gln Leu Gly Leu
                325                 330                 335

Ala Phe Leu Arg Gly Leu Ser Tyr His Asp Gly Ala Leu Val Val Thr
                340                 345                 350

Lys Ala Gly Tyr Tyr Tyr Ile Tyr Ser Lys Val Gln Leu Gly Gly Val
            355                 360                 365

Gly Cys Pro Leu Gly Leu Ala Ser Thr Ile Thr His Gly Leu Tyr Lys
        370                 375                 380

Arg Thr Pro Arg Tyr Pro Glu Glu Leu Glu Leu Leu Val Ser Gln Gln
385                 390                 395                 400

Ser Pro Cys Gly Arg Ala Thr Ser Ser Ser Arg Val Trp Trp Asp Ser
                405                 410                 415

Ser Phe Leu Gly Gly Val Val His Leu Glu Ala Gly Glu Glu Val Val
                420                 425                 430

Val Arg Val Leu Asp Glu Arg Leu Val Arg Leu Arg Asp Gly Thr Arg
            435                 440                 445

Ser Tyr Phe Gly Ala Phe Met Val Gly Ser Ser Ser Ser Ser Gly Ser
            450                 455                 460

Cys Asp Lys Thr His Thr Cys Pro Pro Cys Pro Ala Pro Glu Leu Leu
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
                500                 505                 510

His Glu Asp Pro Glu Val Lys Phe Asn Trp Tyr Val Asp Gly Val Glu
                515                 520                 525

Val His Asn Ala Lys Thr Lys Pro Arg Glu Glu Gln Tyr Ser Ser Thr
            530                 535                 540
```

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Pro Ala Pro
                565                 570                 575

Ile Glu Lys Thr Ile Ser Lys Ala Lys Gly Gln Pro Arg Glu Pro Gln
            580                 585                 590

Val Tyr Thr Leu Pro Pro Ser Arg Glu Glu Met Thr Lys Asn Gln Val
        595                 600                 605

Ser Leu Thr Cys Leu Val Lys Gly Phe Tyr Pro Ser Asp Ile Ala Val
610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
        675                 680                 685

Ser Pro Gly Lys
    690

<210> SEQ ID NO 33
<211> LENGTH: 699
<212> TYPE: PRT
<213> ORGANISM: Artificial Sequence
<220> FEATURE:
<223> OTHER INFORMATION: Configuration with deletion of N93 in RBD 2 and
      3

<400> SEQUENCE: 33

Glu Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30

Leu Arg Gly Leu Ser Tyr His Asp Gly Ala Leu Val Val Thr Lys Ala
        35                  40                  45

Gly Tyr Tyr Tyr Ile Tyr Ser Lys Val Gln Leu Gly Gly Val Gly Cys
    50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Ser Arg Val Trp Trp Asp Ser Ser Phe
            100                 105                 110

Leu Gly Gly Val Val His Leu Glu Ala Gly Glu Glu Val Val Val Arg
        115                 120                 125

Val Leu Asp Glu Arg Leu Val Arg Leu Arg Asp Gly Thr Arg Ser Tyr
    130                 135                 140

Phe Gly Ala Phe Met Val Gly Ser Gly Ser Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
            180                 185                 190

Tyr His Asp Gly Ala Leu Val Val Thr Lys Ala Gly Tyr Tyr Tyr Ile

-continued

```
            195                 200                 205
Tyr Ser Lys Val Gln Leu Gly Gly Val Gly Cys Pro Leu Gly Leu Ala
    210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
            260                 265                 270

His Leu Glu Ala Gly Glu Val Val Arg Val Leu Asp Glu Arg
        275                 280                 285

Leu Val Arg Leu Arg Asp Gly Thr Arg Ser Tyr Phe Gly Ala Phe Met
    290                 295                 300

Val Gly Ser Gly Ser Gly Asn Gly Ser Pro Ala Ala His Leu Thr Gly
305                 310                 315                 320

Ala Asn Ser Ser Leu Thr Gly Ser Gly Gly Pro Leu Leu Trp Glu Thr
                325                 330                 335

Gln Leu Gly Leu Ala Phe Leu Arg Gly Leu Ser Tyr His Asp Gly Ala
            340                 345                 350

Leu Val Val Thr Lys Ala Gly Tyr Tyr Tyr Ile Tyr Ser Lys Val Gln
        355                 360                 365

Leu Gly Gly Val Gly Cys Pro Leu Gly Leu Ala Ser Thr Ile Thr His
    370                 375                 380

Gly Leu Tyr Lys Arg Thr Pro Arg Tyr Pro Glu Glu Leu Glu Leu Leu
385                 390                 395                 400

Val Ser Gln Gln Ser Pro Cys Gly Arg Ala Thr Ser Ser Ser Arg Val
                405                 410                 415

Trp Trp Asp Ser Ser Phe Leu Gly Gly Val Val His Leu Glu Ala Gly
            420                 425                 430

Glu Glu Val Val Arg Val Leu Asp Glu Arg Leu Val Arg Leu Arg
        435                 440                 445

Asp Gly Thr Arg Ser Tyr Phe Gly Ala Phe Met Val Gly Ser Ser Ser
    450                 455                 460

Ser Ser Ser Ser Gly Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Ser Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Thr Cys Leu Val Lys Gly Phe
    610                 615                 620
```

```
Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
            645                 650                 655

Phe Leu Tyr Ser Lys Leu Thr Val Asp Lys Ser Arg Trp Gln Gln Gly
        660                 665                 670

Asn Val Phe Ser Cys Ser Val Met His Glu Ala Leu His Asn His Tyr
    675                 680                 685

Thr Gln Lys Ser Leu Ser Leu Ser Pro Gly Lys
690                 695
```

<210> SEQ ID NO 34
<211> LENGTH: 699
<212> TYPE: PRT
<213> ORGANISM: Artificial Sequence
<220> FEATURE:
<223> OTHER INFORMATION: Configuration: SEQ33 with N terminal amino acid
      exchange E1Q

<400> SEQUENCE: 34

```
Gln Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30

Leu Arg Gly Leu Ser Tyr His Asp Gly Ala Leu Val Val Thr Lys Ala
        35                  40                  45

Gly Tyr Tyr Tyr Ile Tyr Ser Lys Val Gln Leu Gly Val Gly Cys
50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Arg Val Trp Trp Asp Ser Ser Phe
            100                 105                 110

Leu Gly Gly Val Val His Leu Glu Ala Gly Glu Glu Val Val Val Arg
        115                 120                 125

Val Leu Asp Glu Arg Leu Val Arg Leu Arg Asp Gly Thr Arg Ser Tyr
130                 135                 140

Phe Gly Ala Phe Met Val Gly Ser Gly Ser Gly Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
            180                 185                 190

Tyr His Asp Gly Ala Leu Val Val Thr Lys Ala Gly Tyr Tyr Tyr Ile
        195                 200                 205

Tyr Ser Lys Val Gln Leu Gly Gly Val Gly Cys Pro Leu Gly Leu Ala
210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
            260                 265                 270

His Leu Glu Ala Gly Glu Glu Val Val Val Arg Val Leu Asp Glu Arg
```

-continued

```
                275                 280                 285
Leu Val Arg Leu Arg Asp Gly Thr Arg Ser Tyr Phe Gly Ala Phe Met
290                 295                 300

Val Gly Ser Gly Ser Gly Asn Gly Ser Pro Ala Ala His Leu Thr Gly
305                 310                 315                 320

Ala Asn Ser Ser Leu Thr Gly Ser Gly Gly Pro Leu Leu Trp Glu Thr
                325                 330                 335

Gln Leu Gly Leu Ala Phe Leu Arg Gly Leu Ser Tyr His Asp Gly Ala
                340                 345                 350

Leu Val Val Thr Lys Ala Gly Tyr Tyr Tyr Ile Tyr Ser Lys Val Gln
                355                 360                 365

Leu Gly Gly Val Gly Cys Pro Leu Gly Leu Ala Ser Thr Ile Thr His
370                 375                 380

Gly Leu Tyr Lys Arg Thr Pro Arg Tyr Pro Glu Glu Leu Glu Leu Leu
385                 390                 395                 400

Val Ser Gln Gln Ser Pro Cys Gly Arg Ala Thr Ser Ser Ser Arg Val
                405                 410                 415

Trp Trp Asp Ser Ser Phe Leu Gly Gly Val Val His Leu Glu Ala Gly
                420                 425                 430

Glu Glu Val Val Val Arg Val Leu Asp Glu Arg Leu Val Arg Leu Arg
                435                 440                 445

Asp Gly Thr Arg Ser Tyr Phe Gly Ala Phe Met Val Gly Ser Ser Ser
450                 455                 460

Ser Ser Ser Ser Ser Gly Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
                500                 505                 510

Cys Val Val Val Asp Val Ser His Glu Asp Pro Glu Val Lys Phe Asn
                515                 520                 525

Trp Tyr Val Asp Gly Val Glu Val His Asn Ala Lys Thr Lys Pro Arg
530                 535                 540

Glu Glu Gln Tyr Ser Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
                580                 585                 590

Gly Gln Pro Arg Glu Pro Gln Val Tyr Thr Leu Pro Pro Ser Arg Glu
                595                 600                 605

Glu Met Thr Lys Asn Gln Val Ser Leu Thr Cys Leu Val Lys Gly Phe
610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
                660                 665                 670

Asn Val Phe Ser Cys Ser Val Met His Glu Ala Leu His Asn His Tyr
                675                 680                 685

Thr Gln Lys Ser Leu Ser Leu Ser Pro Gly Lys
                690                 695
```

```
<210> SEQ ID NO 35
<211> LENGTH: 696
<212> TYPE: PRT
<213> ORGANISM: Artificial Sequence
<220> FEATURE:
<223> OTHER INFORMATION: Configuration: Seq33 with shorter hinge linker

<400> SEQUENCE: 35
```

| | | | | | | | | | | | | | | | |
|---|---|---|---|---|---|---|---|---|---|---|---|---|---|---|---|
| Glu | Val | Asn | Pro | Ala | Ala | His | Leu | Thr | Gly | Ala | Asn | Ser | Ser | Leu | Thr |
| 1 | | | | 5 | | | | | 10 | | | | | 15 | |
| Gly | Ser | Gly | Gly | Pro | Leu | Leu | Trp | Glu | Thr | Gln | Leu | Gly | Leu | Ala | Phe |
| | | | 20 | | | | | 25 | | | | | 30 | | |
| Leu | Arg | Gly | Leu | Ser | Tyr | His | Asp | Gly | Ala | Leu | Val | Val | Thr | Lys | Ala |
| | | | 35 | | | | | 40 | | | | | 45 | | |
| Gly | Tyr | Tyr | Tyr | Ile | Tyr | Ser | Lys | Val | Gln | Leu | Gly | Val | Gly | Cys |
| | 50 | | | | | 55 | | | | | 60 | | | |
| Pro | Leu | Gly | Leu | Ala | Ser | Thr | Ile | Thr | His | Gly | Leu | Tyr | Lys | Arg | Thr |
| 65 | | | | | 70 | | | | | 75 | | | | | 80 |
| Pro | Arg | Tyr | Pro | Glu | Glu | Leu | Glu | Leu | Leu | Val | Ser | Gln | Gln | Ser | Pro |
| | | | | 85 | | | | | 90 | | | | | 95 | |
| Cys | Gly | Arg | Ala | Thr | Ser | Ser | Ser | Arg | Val | Trp | Trp | Asp | Ser | Ser | Phe |
| | | | | 100 | | | | | 105 | | | | | 110 | |
| Leu | Gly | Gly | Val | Val | His | Leu | Glu | Ala | Gly | Glu | Val | Val | Arg |
| | | | | 115 | | | | | 120 | | | | | 125 |
| Val | Leu | Asp | Glu | Arg | Leu | Val | Arg | Leu | Arg | Asp | Gly | Thr | Arg | Ser | Tyr |
| | 130 | | | | | 135 | | | | | 140 | | | | |
| Phe | Gly | Ala | Phe | Met | Val | Gly | Ser | Gly | Ser | Gly | Asn | Gly | Ser | Pro | Ala |
| 145 | | | | | 150 | | | | | 155 | | | | | 160 |
| Ala | His | Leu | Thr | Gly | Ala | Asn | Ser | Ser | Leu | Thr | Gly | Ser | Gly | Gly | Pro |
| | | | | 165 | | | | | 170 | | | | | 175 | |
| Leu | Leu | Trp | Glu | Thr | Gln | Leu | Gly | Leu | Ala | Phe | Leu | Arg | Gly | Leu | Ser |
| | | | | 180 | | | | | 185 | | | | | 190 | |
| Tyr | His | Asp | Gly | Ala | Leu | Val | Val | Thr | Lys | Ala | Gly | Tyr | Tyr | Tyr | Ile |
| | | | | 195 | | | | | 200 | | | | | 205 | |
| Tyr | Ser | Lys | Val | Gln | Leu | Gly | Val | Gly | Cys | Pro | Leu | Gly | Leu | Ala |
| | 210 | | | | | 215 | | | | | 220 | | | |
| Ser | Thr | Ile | Thr | His | Gly | Leu | Tyr | Lys | Arg | Thr | Pro | Arg | Tyr | Pro | Glu |
| 225 | | | | | 230 | | | | | 235 | | | | | 240 |
| Glu | Leu | Glu | Leu | Leu | Val | Ser | Gln | Gln | Ser | Pro | Cys | Gly | Arg | Ala | Thr |
| | | | | 245 | | | | | 250 | | | | | 255 | |
| Ser | Ser | Ser | Arg | Val | Trp | Trp | Asp | Ser | Ser | Phe | Leu | Gly | Gly | Val | Val |
| | | | | 260 | | | | | 265 | | | | | 270 | |
| His | Leu | Glu | Ala | Gly | Glu | Val | Val | Arg | Val | Leu | Asp | Glu | Arg |
| | | | | 275 | | | | | 280 | | | | | 285 |
| Leu | Val | Arg | Leu | Arg | Asp | Gly | Thr | Arg | Ser | Tyr | Phe | Gly | Ala | Phe | Met |
| | | | | 290 | | | | | 295 | | | | | 300 | |
| Val | Gly | Ser | Gly | Ser | Gly | Asn | Gly | Ser | Pro | Ala | Ala | His | Leu | Thr | Gly |
| 305 | | | | | 310 | | | | | 315 | | | | | 320 |
| Ala | Asn | Ser | Ser | Leu | Thr | Gly | Ser | Gly | Gly | Pro | Leu | Leu | Trp | Glu | Thr |
| | | | | 325 | | | | | 330 | | | | | 335 | |
| Gln | Leu | Gly | Leu | Ala | Phe | Leu | Arg | Gly | Leu | Ser | Tyr | His | Asp | Gly | Ala |
| | | | | 340 | | | | | 345 | | | | | 350 | |
| Leu | Val | Val | Thr | Lys | Ala | Gly | Tyr | Tyr | Tyr | Ile | Tyr | Ser | Lys | Val | Gln |
| | | | | 355 | | | | | 360 | | | | | 365 | |

-continued

Leu Gly Gly Val Gly Cys Pro Leu Gly Leu Ala Ser Thr Ile Thr His
                370                 375                 380

Gly Leu Tyr Lys Arg Thr Pro Arg Tyr Pro Glu Leu Glu Leu Leu
385                 390                 395                 400

Val Ser Gln Gln Ser Pro Cys Gly Arg Ala Thr Ser Ser Arg Val
            405                 410                 415

Trp Trp Asp Ser Ser Phe Leu Gly Gly Val Val His Leu Glu Ala Gly
                420                 425                 430

Glu Glu Val Val Val Arg Val Leu Asp Glu Arg Leu Val Arg Leu Arg
                435                 440                 445

Asp Gly Thr Arg Ser Tyr Phe Gly Ala Phe Met Val Gly Ser Ser Ser
    450                 455                 460

Ser Ser Gly Ser Cys Asp Lys Thr His Thr Cys Pro Pro Cys Pro Ala
465                 470                 475                 480

Pro Glu Leu Leu Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
                500                 505                 510

Val Asp Val Ser His Glu Asp Pro Glu Val Lys Phe Asn Trp Tyr Val
            515                 520                 525

Asp Gly Val Glu Val His Asn Ala Lys Thr Lys Pro Arg Glu Glu Gln
    530                 535                 540

Tyr Ser Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Pro Ala Pro Ile Glu Lys Thr Ile Ser Lys Ala Lys Gly Gln Pro
            580                 585                 590

Arg Glu Pro Gln Val Tyr Thr Leu Pro Pro Ser Arg Glu Glu Met Thr
    595                 600                 605

Lys Asn Gln Val Ser Leu Thr Cys Leu Val Lys Gly Phe Tyr Pro Ser
610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Lys Leu Thr Val Asp Lys Ser Arg Trp Gln Gln Gly Asn Val Phe
            660                 665                 670

Ser Cys Ser Val Met His Glu Ala Leu His Asn His Tyr Thr Gln Lys
    675                 680                 685

Ser Leu Ser Leu Ser Pro Gly Lys
   690                 695

<210> SEQ ID NO 36
<211> LENGTH: 456
<212> TYPE: PRT
<213> ORGANISM: Artificial Sequence
<220> FEATURE:
<223> OTHER INFORMATION: Exemplary scLIGHT-RBD module

<400> SEQUENCE: 36

Glu Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
                20                  25                  30

```
Leu Arg Gly Leu Ser Tyr His Asp Gly Ala Leu Val Val Thr Lys Ala
            35                  40                  45

Gly Tyr Tyr Ile Tyr Ser Lys Val Gln Leu Gly Gly Val Gly Cys
    50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Ser Arg Val Trp Trp Asp Ser Ser Phe
                100                 105                 110

Leu Gly Gly Val Val His Leu Glu Ala Gly Glu Glu Val Val Val Arg
            115                 120                 125

Val Leu Asp Glu Arg Leu Val Arg Leu Arg Asp Gly Thr Arg Ser Tyr
            130                 135                 140

Phe Gly Ala Phe Met Val Gly Ser Gly Ser Gly Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
            180                 185                 190

Tyr His Asp Gly Ala Leu Val Val Thr Lys Ala Gly Tyr Tyr Ile
            195                 200                 205

Tyr Ser Lys Val Gln Leu Gly Gly Val Gly Cys Pro Leu Gly Leu Ala
    210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
                260                 265                 270

His Leu Glu Ala Gly Glu Glu Val Val Val Arg Val Leu Asp Glu Arg
            275                 280                 285

Leu Val Arg Leu Arg Asp Gly Thr Arg Ser Tyr Phe Gly Ala Phe Met
            290                 295                 300

Val Gly Ser Gly Ser Pro Ala Ala His Leu Thr Gly Ala Asn Ser Ser
305                 310                 315                 320

Leu Thr Gly Ser Gly Gly Pro Leu Leu Trp Glu Thr Gln Leu Gly Leu
                325                 330                 335

Ala Phe Leu Arg Gly Leu Ser Tyr His Asp Gly Ala Leu Val Val Thr
                340                 345                 350

Lys Ala Gly Tyr Tyr Ile Tyr Ser Lys Val Gln Leu Gly Gly Val
                355                 360                 365

Gly Cys Pro Leu Gly Leu Ala Ser Thr Ile Thr His Gly Leu Tyr Lys
    370                 375                 380

Arg Thr Pro Arg Tyr Pro Glu Glu Leu Glu Leu Leu Val Ser Gln Gln
385                 390                 395                 400

Ser Pro Cys Gly Arg Ala Thr Ser Ser Ser Arg Val Trp Trp Asp Ser
                405                 410                 415

Ser Phe Leu Gly Gly Val Val His Leu Glu Ala Gly Glu Glu Val Val
                420                 425                 430

Val Arg Val Leu Asp Glu Arg Leu Val Arg Leu Arg Asp Gly Thr Arg
                435                 440                 445
```

Ser Tyr Phe Gly Ala Phe Met Val
    450                 455

<210> SEQ ID NO 37
<211> LENGTH: 2192
<212> TYPE: DNA
<213> ORGANISM: Artificial Sequence
<220> FEATURE:
<223> OTHER INFORMATION: DNA sequence encoding PROTEIN A (Seq25)

<400> SEQUENCE: 37

| | | | | |
|---|---|---|---|---|
| aagctttagg | gataacaggg | taatagccgc | caccatggag | actgacaccc tgctggtgtt | 60 |
| cgtgctgctg | gtctgggtgc | ctgcaggaaa | tggagaagtg | aaccccgccg cccatctgac | 120 |
| cggcgctaac | agcagcctga | caggttctgg | cggacccctc | tgtgggaga cacaactggg | 180 |
| cctggccttc | ctgaggggcc | tgagctacca | tgatggcgcc | ctggtggtga ccaaggccgg | 240 |
| ctactactac | atctattcca | aggtccagct | cggaggcgtg | ggatgccctc tgggactggc | 300 |
| ctccaccatc | acccacggcc | tgtacaagcg | gaccccctagg | taccccgagg aactggaact | 360 |
| gctcgtctcc | aacagagcc | cttgcggcag | ggctacctcc | tccagcaggg tgtggtggga | 420 |
| ctccagcttc | ctgggaggcg | tcgtccacct | ggaggctgga | gaagaagtgg tggtgcgggt | 480 |
| cctggacgaa | aggctggtga | ggctcaggga | cggcacccgg | tcctacttg gagcctttat | 540 |
| ggtgggctcc | ggatctggta | acggcagccc | cgctgctcat | ctgacaggcg ccaatagcag | 600 |
| cctgacaggc | agcggaggcc | ctctgctgtg | gaaacacag | ctgggcctgg cctttctgag | 660 |
| gggcctgtcc | tatcacgatg | gagccctggt | ggtgaccaaa | gccggctatt actatatcta | 720 |
| cagcaaggtg | cagctgggcg | gagtgggatg | tcctctgggc | ctggcctcca ccatcacaca | 780 |
| cggactgtat | aagcggacac | ctaggtatcc | cgaagagctg | gagctcctgg tgtcccagca | 840 |
| aagcccttgt | ggaagggcta | cctccagcag | cagggtctgg | tgggactcct ccttcctggg | 900 |
| cggcgtggtc | catctggaag | ctggcgagga | ggtggtggtg | agggtcctgg atgagaggct | 960 |
| ggtcaggctg | agggatggca | cccggtccta | ttttggcgct | ttcatggtgg gctctggtag | 1020 |
| ccctgccgcc | cacctgacag | gagccaacag | cagcctgaca | ggaagcggcg gccctctgct | 1080 |
| gtgggagacc | caactgggcc | tggccttcct | gcggggcctc | tcctaccacg acggcgctct | 1140 |
| ggtggtgacc | aaggccggct | attattatat | ctactccaaa | gtccagctgg gaggcgtcgg | 1200 |
| ctgtcctctc | ggactggctt | ccaccatcac | ccatggcctg | tacaaagga cccctaggta | 1260 |
| ccccgaagag | ttagaactgc | tggtctccca | gcagtcccct | tgcggaaggg ccacaagcag | 1320 |
| cagccgggtg | tggtgggact | ccagctttct | gggcggagtg | gtgcacctgg aagcggaga | 1380 |
| ggaggtcgtg | gtcagggtcc | tggatgaaag | gctggtgcgg | ctgagggatg caccaggtc | 1440 |
| ctatttcggc | gccttcatgg | tcggatcctc | gagttcatcg | tcctcatccg gctcatgtga | 1500 |
| taagacccac | acctgccctc | cctgtcctgc | ccctgagctg | ctgggcggac cttctgtgtt | 1560 |
| cctgttcccc | cccaagccta | aggacaccct | gatgatctcc | aggaccctg aggtgacctg | 1620 |
| tgtggtggtg | gacgtgtctc | acgaagatcc | cgaggtgaag | ttcaactggt acgtggacgg | 1680 |
| cgtggaggtc | cacaacgcca | agaccaagcc | tagggaggag | cagtacagct ccacctaccg | 1740 |
| ggtggtgtct | gtgctgaccg | tgctgcacca | ggattggctg | aacggaaagg agtataagtg | 1800 |
| taaggtctcc | aacaaggccc | tgcctgccc | catcgagaaa | accatctcca aggccaaggg | 1860 |
| ccagcctcgg | gagcctcagg | tgtacaccct | gcctcctagc | agggaggaga tgaccaagaa | 1920 |
| ccaggtgtcc | ctgacctgtc | tggtgaaggg | cttctacccct | tccgatatcg ccgtggagtg | 1980 |

```
ggagtctaat ggccagcccg agaacaacta caagaccacc cctcctgtgc tggactctga    2040
cggctccttc ttcctgtact ccaagctgac cgtggacaag tccagatggc agcagggcaa    2100
cgtgttctcc tgctccgtga tgcacgaggc cctgcacaat cactacaccc agaagtccct    2160
gtctctgagt ccgggcaagt aataggcgcg cc                                   2192
```

<210> SEQ ID NO 38
<211> LENGTH: 227
<212> TYPE: PRT
<213> ORGANISM: Artificial Sequence
<220> FEATURE:
<223> OTHER INFORMATION: LIGHT-RBD fused to RB69 FOLDON (PROTEIN X)

<400> SEQUENCE: 38

```
Met Glu Thr Asp Thr Leu Leu Val Phe Val Leu Leu Val Trp Val Pro
1               5                   10                  15

Ala Gly Asn Gly Glu Val Asn Pro Ala Ala His Leu Thr Gly Ala As

```
Leu Arg Gly Leu Ser Tyr His Asp Gly Ala Leu Val Thr Lys Ala
         35                  40                  45

Gly Tyr Tyr Tyr Ile Tyr Ser Lys Val Gln Leu Gly Gly Val Gly Cys
 50                  55                  60

Pro Leu Gly Leu Ala Ser Thr Ile Thr His Gly Leu Tyr Lys Arg Thr
 65                  70                  75                  80

Pro Arg Tyr Pro Glu Glu Leu Glu Leu Leu Val Ser Gln Gln Ser Pro
                 85                  90                  95

Cys Gly Arg Ala Thr Ser Ser Ser Arg Val Trp Trp Asp Ser Ser Phe
                100                 105                 110

Leu Gly Gly Val Val His Leu Glu Ala Gly Glu Glu Val Val Val Arg
            115                 120                 125

Val Leu Asp Glu Arg Leu Val Arg Leu Arg Asp Gly Thr Arg Ser Tyr
        130                 135                 140

Phe Gly Ala Phe Met Val Gly Ser Gly Ser Gly Asn Gly Ser Asn Pro
145                 150                 155                 160

Ala Ala His Leu Thr Gly Ala Asn Ser Ser Leu Thr Gly Ser Gly Gly
                165                 170                 175

Pro Leu Leu Trp Glu Thr Gln Leu Gly Leu Ala Phe Leu Arg Gly Leu
            180                 185                 190

Ser Tyr His Asp Gly Ala Leu Val Val Thr Lys Ala Gly Tyr Tyr Tyr
        195                 200                 205

Ile Tyr Ser Lys Val Gln Leu Gly Gly Val Gly Cys Pro Leu Gly Leu
    210                 215                 220

Ala Ser Thr Ile Thr His Gly Leu Tyr Lys Arg Thr Pro Arg Tyr Pro
225                 230                 235                 240

Glu Glu Leu Glu Leu Leu Val Ser Gln Gln Ser Pro Cys Gly Arg Ala
                245                 250                 255

Thr Ser Ser Ser Arg Val Trp Trp Asp Ser Ser Phe Leu Gly Gly Val
            260                 265                 270

Val His Leu Glu Ala Gly Glu Glu Val Val Val Arg Val Leu Asp Glu
        275                 280                 285

Arg Leu Val Arg Leu Arg Asp Gly Thr Arg Ser Tyr Phe Gly Ala Phe
    290                 295                 300

Met Val Gly Ser Gly Ser Gly Asn Gly Ser Asn Pro Ala Ala His Leu
305                 310                 315                 320

Thr Gly Ala Asn Ser Ser Leu Thr Gly Ser Gly Gly Pro Leu Leu Trp
                325                 330                 335

Glu Thr Gln Leu Gly Leu Ala Phe Leu Arg Gly Leu Ser Tyr His Asp
            340                 345                 350

Gly Ala Leu Val Val Thr Lys Ala Gly Tyr Tyr Tyr Ile Tyr Ser Lys
        355                 360                 365

Val Gln Leu Gly Gly Val Gly Cys Pro Leu Gly Leu Ala Ser Thr Ile
    370                 375                 380

Thr His Gly Leu Tyr Lys Arg Thr Pro Arg Tyr Pro Glu Glu Leu Glu
385                 390                 395                 400

Leu Leu Val Ser Gln Gln Ser Pro Cys Gly Arg Ala Thr Ser Ser Ser
                405                 410                 415

Arg Val Trp Trp Asp Ser Ser Phe Leu Gly Gly Val Val His Leu Glu
            420                 425                 430

Ala Gly Glu Glu Val Val Val Arg Val Leu Asp Glu Arg Leu Val Arg
        435                 440                 445

Leu Arg Asp Gly Thr Arg Ser Tyr Phe Gly Ala Phe Met Val
```

<210> SEQ ID NO 40
<211> LENGTH: 460
<212> TYPE: PRT
<213> ORGANISM: Artificial Sequence
<220> FEATURE:
<223> OTHER INFORMATION: Exemplary scLIGHT-RBD module

<400> SEQUENCE: 40

```
Glu Val Asn Pro Ala Ala His Leu Thr Gly Ala Asn Ser Ser Leu Thr
1               5                   10                  15

Gly Ser Gly Gly Pro Leu Leu Trp Glu Thr Gln Leu Gly Leu Ala Phe
            20                  25                  30

Leu Arg Gly Leu Ser Tyr His Asp Gly Ala Leu Val Val Thr Lys Ala
        35                  40                  45

Gly Tyr Tyr Tyr Ile Tyr Ser Lys Val Gln Leu Gly Gly Val Gly Cys
    50                  55                  60

Pro Leu Gly Leu Ala Ser Thr Ile Thr His Gly Leu Tyr Lys Arg Thr
65                  70                  75                  80

Pro Arg Tyr Pro Glu Glu Leu Glu Leu Leu Val Ser Gln Gln Ser Pro
                85                  90                  95

Cys Gly Arg Ala Thr Ser Ser Ser Arg Val Trp Trp Asp Ser Ser Phe
            100                 105                 110

Leu Gly Gly Val Val His Leu Glu Ala Gly Glu Glu Val Val Val Arg
        115                 120                 125

Val Leu Asp Glu Arg Leu Val Arg Leu Arg Asp Gly Thr Arg Ser Tyr
    130                 135                 140

Phe Gly Ala Phe Met Val Gly Ser Gly Ser Gly Asn Gly Ser Pro Ala
145                 150                 155                 160

Ala His Leu Thr Gly Ala Asn Ser Ser Leu Thr Gly Ser Gly Gly Pro
                165                 170                 175

Leu Leu Trp Glu Thr Gln Leu Gly Leu Ala Phe Leu Arg Gly Leu Ser
            180                 185                 190

Tyr His Asp Gly Ala Leu Val Val Thr Lys Ala Gly Tyr Tyr Tyr Ile
        195                 200                 205

Tyr Ser Lys Val Gln Leu Gly Gly Val Gly Cys Pro Leu Gly Leu Ala
    210                 215                 220

Ser Thr Ile Thr His Gly Leu Tyr Lys Arg Thr Pro Arg Tyr Pro Glu
225                 230                 235                 240

Glu Leu Glu Leu Leu Val Ser Gln Gln Ser Pro Cys Gly Arg Ala Thr
                245                 250                 255

Ser Ser Ser Arg Val Trp Trp Asp Ser Ser Phe Leu Gly Gly Val Val
            260                 265                 270

His Leu Glu Ala Gly Glu Glu Val Val Val Arg Val Leu Asp Glu Arg
        275                 280                 285

Leu Val Arg Leu Arg Asp Gly Thr Arg Ser Tyr Phe Gly Ala Phe Met
    290                 295                 300

Val Gly Ser Gly Ser Gly Asn Gly Ser Pro Ala Ala His Leu Thr Gly
305                 310                 315                 320

Ala Asn Ser Ser Leu Thr Gly Ser Gly Gly Pro Leu Leu Trp Glu Thr
                325                 330                 335

Gln Leu Gly Leu Ala Phe Leu Arg Gly Leu Ser Tyr His Asp Gly Ala
            340                 345                 350

Leu Val Val Thr Lys Ala Gly Tyr Tyr Tyr Ile Tyr Ser Lys Val Gln
```

-continued

```
              355                 360                 365
Leu Gly Gly Val Gly Cys Pro Leu Gly Leu Ala Ser Thr Ile Thr His
        370                 375                 380

Gly Leu Tyr Lys Arg Thr Pro Arg Tyr Pro Glu Glu Leu Glu Leu Leu
385                 390                 395                 400

Val Ser Gln Gln Ser Pro Cys Gly Arg Ala Thr Ser Ser Ser Arg Val
                405                 410                 415

Trp Trp Asp Ser Ser Phe Leu Gly Gly Val Val His Leu Glu Ala Gly
            420                 425                 430

Glu Glu Val Val Val Arg Val Leu Asp Glu Arg Leu Val Arg Leu Arg
        435                 440                 445

Asp Gly Thr Arg Ser Tyr Phe Gly Ala Phe Met Val
        450                 455                 460
```